(12) United States Patent
Fieldhouse et al.

(10) Patent No.: US 9,790,220 B2
(45) Date of Patent: Oct. 17, 2017

(54) SUBSTITUTED CYCLOPENTANES, TETRAHYDROFURANES AND PYRROLIDINES AS OREXIN RECEPTOR ANTAGONISTS

(71) Applicant: Takeda Pharmaceutical Company Limited, Osaka-Shi (JP)

(72) Inventors: Charlotte Fieldhouse, Cambridgeshire (GB); Angela Glen, Cambridgeshire (GB); Tatsuhiko Fujimoto, Kanagawa (JP); John Stephen Robinson, Cambridgeshire (GB)

(73) Assignee: Takeda Pharmaceutical Company Limited (JP)

( * ) Notice: Subject to any disclaimer, the term of this patent is extended or adjusted under 35 U.S.C. 154(b) by 0 days.

(21) Appl. No.: 15/120,002

(22) PCT Filed: Feb. 19, 2015

(86) PCT No.: PCT/GB2015/050482
§ 371 (c)(1),
(2) Date: Aug. 18, 2016

(87) PCT Pub. No.: WO2015/124934
PCT Pub. Date: Aug. 27, 2015

(65) Prior Publication Data
US 2017/0073340 A1 Mar. 16, 2017

(30) Foreign Application Priority Data
Feb. 20, 2014 (EP) ..................................... 14156010

(51) Int. Cl.
| | | |
|---|---|---|
| *A61K 31/015* | (2006.01) | |
| *A61K 31/16* | (2006.01) | |
| *C07D 417/14* | (2006.01) | |
| *C07D 401/12* | (2006.01) | |
| *C07D 413/12* | (2006.01) | |
| *C07D 417/12* | (2006.01) | |
| *A61K 31/4439* | (2006.01) | |
| *A61K 31/4545* | (2006.01) | |
| *A61K 31/4709* | (2006.01) | |
| *A61K 31/498* | (2006.01) | |

(52) U.S. Cl.
CPC .......... *C07D 417/14* (2013.01); *A61K 31/015* (2013.01); *A61K 31/16* (2013.01); *A61K 31/4439* (2013.01); *A61K 31/4545* (2013.01); *A61K 31/4709* (2013.01); *A61K 31/498* (2013.01); *C07D 401/12* (2013.01); *C07D 413/12* (2013.01); *C07D 417/12* (2013.01)

(58) Field of Classification Search
CPC .............................. A61K 31/015; A61K 31/16
See application file for complete search history.

(56) References Cited

FOREIGN PATENT DOCUMENTS

WO WO2008/038841 4/2008

OTHER PUBLICATIONS

Database CA [Online], Chemical Abstracts Service, Columbus, Ohio, US; Palomba, Michele et al: "Anti-inflammatory and analgesic amides. New developments", XP002724962, retrieved from STN Database accession No. 2000:45655, abstract; and Palomba, Michele et al: "Anti-inflammatory and analgesic amides. New developments", Archly Der Pharmazie (Weinheim, Germany), 333(1), 17-26 Goden: Arpmas; ISSN: 0365-6233, 2000, DOI: 10.1002(SIXI) 1521-4184(200001)333:1 17::Aid-Ardp173.0. CO;2-0 10.1002/(SICI) 1521-4184(200001)333:1 17::AID-ARDP173.0.
Rong Jiang et al: "Disubstituted piperidines as potent orexin (hypocretin) receptor antagonists", Bioorganic & Medicinal Chemistry Letters, Pergamon, Amsterdam, NL, vol. 22, No. 12, Apr. 27, 2012 (Apr. 27, 2012), pp. 3890-3894 XP028509301, ISSN: 0960-894X, DOI: 10.1016/J.BMCL.2012.04.122 [retrieved on May 4, 2012], the whole document.
Sifferlen Thierry et al: "Discovery of substituted lactams as novel dual orexin receptor antagonists. Synthesis, preliminary structure-activity relationship studies and efforts towards improved metabolic stability and pharmacokinetic properties. Pa", Bioorganic & Medicinal Chemistry Letters, vol. 24, No. 4, Dec. 30, 2013 (Dec. 30, 2013), pp. 1201-1208, XP028606685, ISSN: 0960-894X, DOI: 10.1016/J.BMCL.2012.12.092, the whole document.
C J Winrow et al: "Discovery and development of orexin receptor antagonists as therapeutics for insomnia", British Journal of Pharmacology, vol. 171, No. 2, Dec. 23, 2013 (Dec. 23, 2013), pp. 283-293, XP055120026, ISSN: 0007-1188, DOI: 10.1111/bph. 12261 Almorexant, SB-649868.
Christopher, John A.: "orexin receptor antagonists", Pharm. Pat. Analyst, vol. 1, No. 3, 2012, pp. 329-346, XP009178221, p. 330; figure 1; compounds 1, 2, p. 335-p. 336; figures 5, 6; compounds 38, 40, 41, 43-54.
International Search Report and Written Opinion, PCT/GB2015/050482, May 19, 2015.
Notification Concerning Transmittal of International Preliminary Report on Patentability Chapter I of the Patent Cooperation Treaty mailed Sep. 1, 2016 for PCT/GB2015/050482 filed Feb. 19, 2015.

*Primary Examiner* — Yong Chong
(74) *Attorney, Agent, or Firm* — Barnes & Thornburg LLP; Scott D. Rothenberger

(57) ABSTRACT

The present invention provides compounds of formula (I) and pharmaceutically acceptable salts thereof, Formula (I) wherein L, X, $R^a$, $R^b$, $R^1$, $R^2$ and $R^3$ are as defined in the specification, processes for their preparation, pharmaceutical compositions containing them and their use in therapy.

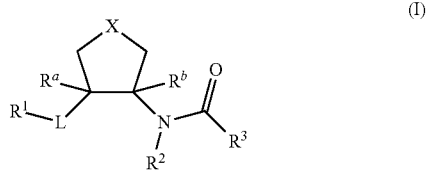

12 Claims, No Drawings

SUBSTITUTED CYCLOPENTANES, TETRAHYDROFURANES AND PYRROLIDINES AS OREXIN RECEPTOR ANTAGONISTS

CROSS-REFERENCE TO RELATED APPLICATIONS

This application is a Section 371 National Stage Application of International No. PCT/GB2015/050482, filed Feb. 19, 2015, and published as WO/2015/124934 A1 on Aug. 27, 2015, which claims priority from EP Patent Application No. 14156010.2, filed Feb. 20, 2014, the contents of which are incorporated herein in their entirety for all purposes.

The present invention relates to amide derivatives, processes for their preparation, pharmaceutical compositions containing them and their use in therapy, particularly in the treatment or prevention of conditions having an association with the orexin sub-type 1 receptor.

The orexin peptides (orexin A and orexin B, OxA and OxB), also known as hypocretins, were discovered in 1998 by two groups (Sakurai et al., *Cell*, 1998, 92, 573 and De Lecea et al., *Proc. Nat. Acad. Sci.*, 1998, 95, 322). These neuropeptides are both derived from the common precursor pre-pro-orexin and are produced in the lateral hypothalamus. OxA is a 33 amino acid residue which has similar potency at both the Ox1R (orexin 1 receptors) and Ox2R (orexin 2 receptors) whereas OxB is made up of 28 amino acids and binds selectively to the Ox2R.

Orexin receptors are believed to be implicated in both feeding behaviour (Sakurai et al., *Cell*, 1998, 92, 573) and also in regulating sleep architecture (Chemelli el al., *Cell*, 1999, 98, 437). More recently, it has been shown that orexin receptors are implicated in arousal, reward, learning and memory (Harris et al., *Trends Neurosci.*, 2006, 29, 571).

WO 2003/099276 describes a broad class of compounds, including certain amides, which are useful as factor Xa inhibitors for treating thromboembolic disorders.

We have now discovered a class of compounds that are orexin receptor antagonists. Furthermore, certain compounds of the invention show selectivity for the orexin 1 receptor over the orexin 2 receptor.

In accordance with the present invention, there is therefore provided a compound of formula

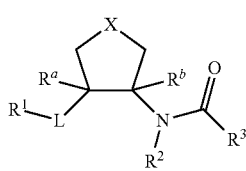

(I)

wherein
$R^1$ represents an 8- to 10-membered fused bicyclic heteroaromatic group optionally substituted by at least one substituent independently selected from halogen, cyano, hydroxyl, $C_3$-$C_6$ cycloalkyl, $C_1$-$C_3$ alkyl, $C_1$-$C_3$ alkoxy, $C_1$-$C_3$ alkoxycarbonyl, $C_1$-$C_3$ alkoxycarbonylamino, $C_1$-$C_3$ haloalkoxy, —$NR^4R^5$, $C_3$-$C_6$ cycloalkylamino, $C_1$-$C_3$ alkylcarbonyloxy, $C_1$-$C_3$ alkylcarbonylamino, sulphonamido (—$SO_2NH_2$), $C_1$-$C_3$ alkylsulphonyl, $C_1$-$C_3$ alkylsulphonylamino and —$C(O)NR^6R^7$;

L represents a bond, $CH_2$, O, NH or $N(CH_3)$;
$R^a$ represents a hydrogen atom or a $C_1$-$C_3$ alkyl or $C_1$-$C_3$ haloalkyl group;
$R^b$ represents a hydrogen atom or a $C_1$-$C_3$ alkyl or $C_1$-$C_3$ haloalkyl group;
X represents $CF_2$, $CHR^8$, O or $NC(O)R^9$;
$R^2$ represents a hydrogen atom or a $C_1$-$C_6$ alkyl or $C_3$-$C_6$ cycloalkyl group;
$R^3$ represents a 5- or 6-membered monocyclic heteroaromatic group optionally substituted by at least one substituent independently selected from halogen, hydroxyl, cyano, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_2$-$C_4$ alkenyl, $C_1$-$C_3$ alkylcarbonyloxy, $C_1$-$C_3$ alkoxycarbonyl, —$NR^{10}R^{11}$, —$C(O)NR^{12}R^{13}$, $C_3$-$C_6$ cycloalkyl, $C_3$-$C_6$ cycloalkyloxy, $C_3$-$C_6$ cycloalkylmethyl or a 5- or 6-membered heteroaryl group, the heteroaryl group being optionally substituted by at least one substituent independently selected from $C_1$-$C_6$ alkyl, $C_1$-$C_6$ alkoxy and $C_1$-$C_6$ haloalkoxy;
$R^4$ and $R^5$ each independently represent a hydrogen atom or a $C_1$-$C_3$ alkyl or $C_3$-$C_6$ cycloalkyl group, or $R^4$ and $R^5$ may together with the nitrogen atom to which they are attached form a 4- to 7-membered saturated heterocyclic ring optionally substituted by at least one substituent independently selected from halogen, hydroxyl and $C_1$-$C_3$ alkoxy;
$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent independently selected from halogen and hydroxyl;
$R^8$ represents a hydrogen or halogen atom or a hydroxyl group;
$R^9$ represents a $C_1$-$C_6$ alkyl, $C_1$-$C_6$ alkoxy, benzyloxy, $C_6$-$C_{10}$ aryl, or heteroaryl group;
$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent independently selected from halogen, hydroxyl and $C_1$-$C_3$ alkoxy; and
$R^{12}$ and $R^{13}$ each independently represent a hydrogen atom or a $C_1$-$C_3$ alkyl or $C_3$-$C_6$ cycloalkyl group, or $R^{12}$ and $R^{13}$ may together with the nitrogen atom to which they are attached form a 4- to 7-membered saturated heterocyclic ring optionally substituted by at least one substituent independently selected from halogen and hydroxyl;
or a pharmaceutically acceptable salt thereof.

In the context of the present specification, unless otherwise stated, an "alkyl" substituent group or an alkyl moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-meth-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl.

An "alkenyl" substituent group or an alkenyl moiety in a substituent group refers to an unsaturated alkyl group having one or more double bonds. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

A "haloalkyl" or "haloalkoxy" substituent group/moiety comprises at least one halogen atom, e.g. one, two, three, four or five halogen atoms. Examples of $C_1$-$C_6$ haloalkyl and $C_1$-$C_6$ haloalkoxy groups/moieties include fluoromethyl, difluoromethyl, trifluoro ethyl, 2,2,2-trifluoroethyl, pentafluoroethyl, fluoromethoxy, difluoromethoxy and trifluoromethoxy.

It will be understood that if $R^4$ and $R^5$ together with the nitrogen atom to which they are attached form a 4- to 7-membered saturated heterocyclic ring, the heterocyclic ring may contain one or more (e.g. one or two) further ring heteroatoms (e.g. nitrogen, oxygen or sulphur atoms) in addition to the nitrogen atom to which $R^4$ and $R^5$ are attached. However, will be appreciated that the invention does not encompass any unstable ring structures or any O—O, O—S or S—S bonds. If a substituent is present on the ring, it may be attached to any suitable ring atom. Examples of such heterocyclic rings include azetidinyl, pyrrolidinyl, piperidinyl, morpholinyl, thiomorpholinyl, piperazinyl, 1,4-azathianyl, azepanyl and 1,4-oxaazepanyl moieties. Similar comments apply with respect to $R^6$ and $R^7$, $R^{10}$ and $R^{11}$, and $R^{12}$ and $R^{13}$ when they form a 4- to 7-membered saturated heterocyclic ring.

A "$C_6$-$C_{10}$ aryl" group refers to a group derived from an aromatic hydrocarbon containing from six to ten carbon atoms. The aryl group may be monocyclic or polycyclic (e.g. bicyclic) in which the two or more rings are fused, examples of which include phenyl, 1-naphthyl and 2-naphthyl. Also included within the scope of the term "aryl", as it is used herein, is a group in which an aromatic ring is fused to one or more non-aromatic rings as exemplified by indanyl and tetrahydronaphth 1. An aryl group may be bonded at any suitable ring atom.

A "heteroaryl" or "heteroaromatic" group is an aryl group in which from 1 to 4 ring carbon atoms are replaced by heteroatoms independently selected from nitrogen, oxygen and sulphur. The heteroaryl or heteroaromatic group can be bonded at any suitable ring atom (i.e. at any carbon or heteroatom of the ring system). Examples of 5- to 10-membered heteroaryl or heteroaromatic groups include the following:

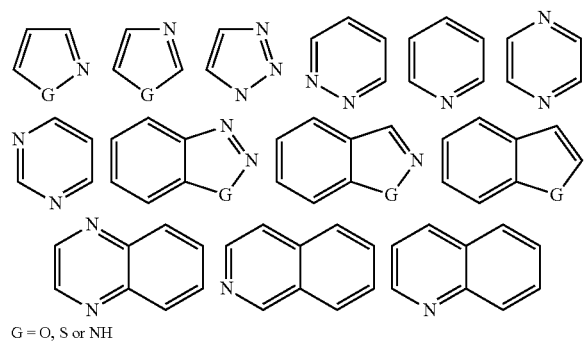

G = O, S or NH

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents an 8-, 9- or 10-membered fused bicyclic heteroaromatic group optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —$NR^4R^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

The fused bicyclic heteroaromatic group in $R^1$ comprises one or more, e.g. one, two, three or four, ring heteroatoms independently selected from nitrogen, oxygen and sulphur. Examples of such heteroaromatic groups include quinoxalinyl, benzothiazolyl, benzoxazolyl, quinolinyl, quinazolinyl, indolyl, 7-azaindolyl, indolizinyl, indazolyl, imidazo[1,2-a]pyridinyl and 7H-pyrrolo[2,3-d]pyrimidinyl.

In an embodiment of the invention, $R^1$ represents a 9- or 10-membered fused bicyclic heteroaromatic group containing one or two ring heteroatoms independently selected from nitrogen, oxygen and sulphur (such as quinoxalinyl, benzothiazolyl, benzoxazolyl, quinolinyl and quinazolinyl), the heteroaromatic group being optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —$NR^4R^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

In another embodiment, $R^1$ represents a 9- or 10-membered fused bicyclic heteroaromatic group containing one or two ring heteroatoms independently selected from nitrogen, oxygen and sulphur (such as quinoxalinyl, benzothiazolyl, benzoxazolyl, quinolinyl and quinazolinyl), the heteroaromatic group being optionally substituted by one, two, three or four substituents independently selected from halogen (e.g. fluorine, chlorine, bromine or iodine), cyano, hydroxyl, $C_5$-$C_6$ cycloalkyl, $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkoxy, —$NR^4R^5$, $C_5$-$C_6$ cycloalkylamino, $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

In a further embodiment, $R^1$ represents a 9- or 10-membered fused bicyclic heteroaromatic group containing one or two ring heteroatoms independently selected from nitrogen, oxygen and sulphur (such as quinoxalinyl, benzothiazolyl, benzoxazolyl, quinolinyl and quinazolinyl), the heteroaromatic group being optionally substituted by one or more (e.g. one or two) halogen, particularly fluorine or chlorine, atoms.

In a still further embodiment, $R^1$ represents any one of the following moieties or is selected from a group containing two or more of such moieties in any combination:
(i) quinoxalin-2-yl,
(ii) 6-fluoro-1,3-benzothiazol-2-yl,
(iii) 5-fluoro-1,3-benzothiazol-2-yl,
(iv) 1,3-benzothiazol-2-yl,
(v) 5-chloro-1,3-benzothiazol-2-yl,
(vi) 1,3-benzoxazol-2-yl,
(vii) 6-chloro-1,3-benzothiazol-2-yl,
(viii) 6-chloro-1,3-benzoxazol-2-yl,
(ix) quinolin-2-yl,
(x) quinazolin-2-yl,
(xi) 6-fluoro-1,3-benzoxazol-2-yl, and
(xii) 5-fluoro-1,3-benzoxazol-2-yl.

In an embodiment of the invention, L represents $CH_2$ or NH.

In a further embodiment, L represents NH.

$R^a$ and $R^b$ each independently represent a hydrogen atom or a $C_1$, $C_2$ or $C_3$ alkyl or $C_1$, $C_2$ or $C_3$ haloalkyl group.

In one embodiment, $R^a$ and $R^b$ each represent a hydrogen atom.

In another embodiment, one of $R^a$ and $R^b$ represents a hydrogen atom and the other of $R^a$ and $R^b$ represents a $C_1$ alkyl (i.e. methyl) or haloalkyl (e.g. trifluoromethyl) group.

In an embodiment of the invention, X represents $CHR^8$.

$R^8$ represents a hydrogen or halogen (e.g. fluorine, chlorine, bromine or iodine) atom or a hydroxyl group.

In one embodiment, $R^8$ represents a hydrogen or fluorine atom or a hydroxyl group.

In another embodiment, $R^8$ represents a hydrogen atom.

$R^2$ represents a hydrogen atom or a $C_1$-$C_6$, or $C_1$-$C_4$, or $C_1$-$C_7$ alkyl or $C_3$-$C_6$ cycloalkyl (cyclopropyl, cyclobutyl, cyclopentyl or cyclohexyl) group.

In one embodiment, $R^2$ represents a hydrogen atom or methyl group.

$R^3$ represents a 5- or 6-membered monocyclic heteroaromatic group optionally substituted by at least one substituent, e.g. one, two, three or four substituents, independently selected from halogen (e.g. fluorine, chlorine, bromine or iodine), hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$, $C_3$ or $C_4$ alkenyl, $C_1$, $C_2$ or $C_3$ alkylcarbonyloxy, $C_1$, $C_2$ or $C_3$ alkoxycarbonyl, —$NR^{10}R^{11}$, —$C(O)NR^{12}R^{13}$, $C_3$-$C_6$ cycloalkyl (cyclopropyl, cyclobutyl, cyclopentyl or cyclohexyl), $C_3$-$C_6$ cycloalkyloxy (cyclopropyloxy, cyclobutyloxy, cyclopentyloxy or cyclohexyloxy), $C_3$-$C_6$ cycloalkylmethyl (cyclopropylmethyl, cyclobutylmethyl, cyclopentylmethyl or cyclohexylmethyl) or a 5- or 6-membered heteroaryl group, the heteroaryl group being optionally substituted by at least one substituent, e.g. one, two, three or four substituents, independently selected from $C_1$-$C_6$ or $C_1$-$C_4$, or $C_1$-$C_2$ alkyl, $C_1$-$C_6$, or $C_1$-$C_4$, or $C_1$-$C_2$ alkoxy and $C_1$-$C_6$, or $C_1$-$C_4$, or $C_1$-$C_2$ haloalkoxy.

$R^3$ represents a 5- or 6-membered monocyclic heteroaromatic group. This $R^3$ heteroaromatic group comprises one or more, e.g. one, two, three or four, ring heteroatoms independently selected from nitrogen, oxygen and sulphur. Examples of such 5- or 6-membered monocyclic heteroaromatic groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl and tetrazinyl.

The $R^3$ heteroaromatic group may optionally be substituted with at least one 5- or 6-membered heteroaryl group.

The term "heteroaryl" group, as used in this context, refers to a monocyclic heteroaromatic group having a total of 5 or 6 ring atoms, of which one, two, three or four ring atoms are heteroatoms independently selected from nitrogen, oxygen and sulphur atoms. Examples of such heteroaryl groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl and tetrazinyl.

In an embodiment of the invention, $R^3$ represents a 5- or 6-membered monocyclic heteroaromatic group containing one or two ring heteroatoms independently selected from nitrogen, oxygen and sulphur (such as pyridinyl, pyrimidinyl and pyrazinyl), the heteroaromatic group being optionally substituted by at least one substituent, e.g. one, three or four substituents, independently selected from fluorine, chlorine, bromine, hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$, $C_3$ or $C_4$ alkenyl, $C_1$, $C_2$ or $C_3$ alkylcarbonyloxy, $C_1$, $C_2$ or $C_3$ alkoxycarbonyl, —$NR^{10}R^{11}$, —$C(O)NR^{12}R^{13}$, $C_3$-$C_5$ cycloalkyl, $C_3$-$C_5$ cycloalkyloxy, $C_3$-$C_5$ cycloalkylmethyl or a 5- or 6-membered heteroaryl group (such as triazolyl, pyrazolyl, oxadiazolyl, pyrimidinyl and imidazolyl), the heteroaryl group being optionally substituted by at least one substituent, e.g. one, two, three or four substituents, independently selected from $C_1$-$C_6$, or $C_1$-$C_4$ or $C_1$-$C_2$ alkyl, $C_1$-$C_6$, or $C_1$-$C_4$ or $C_1$-$C_2$ alkoxy and $C_1$-$C_6$, or $C_1$-$C_4$, or $C_1$-$C_2$ haloalkoxy.

In another embodiment, $R^3$ represents a 5- or 6-membered monocyclic heteroaromatic group containing one or two ring heteroatoms independently selected from nitrogen, oxygen and sulphur (such as pyridinyl, pyrimidinyl and pyrazinyl), the heteroaromatic group being optionally substituted by one, two, three or four substituents independently selected from fluorine, chlorine, bromine, $C_1$, $C_2$ or $C_3$ alkyl, $C_1$, $C_2$ or $C_3$ haloalkyl, $C_1$, $C_2$ or $C_3$ alkoxy, $C_1$, $C_2$ or $C_3$ haloalkoxy, cyclopropyl or a 5- or 6-membered heteroaryl group (such as triazolyl, pyrazolyl, oxadiazolyl, pyrimidinyl and imidazolyl), the heteroaryl group being optionally substituted by at least one substituent, e.g. one, two, three or four substituents, independently selected from $C_1$-$C_2$ alkyl, $C_1$-$C_2$ alkoxy and $C_1$-$C_2$ haloalkoxy.

In a further embodiment, $R^3$ represents a 5- or 6-membered monocyclic heteroaromatic group containing one or two ring heteroatoms independently selected from nitrogen, oxygen and sulphur (such as pyridinyl, pyrimidinyl and pyrazinyl), the heteroaromatic group being optionally substituted by one, two or three (particularly one or two) substituents independently selected from fluorine, chlorine, bromine, $C_1$, $C_2$ or $C_3$ alkyl, $C_1$, $C_2$ or $C_3$ alkoxy, $C_1$, $C_2$ or $C_3$ haloalkoxy, cyclopropyl or a 5- or 6-membered heteroaryl group (such as triazolyl, pyrazolyl, oxadiazolyl, pyrimidinyl and imidazolyl), the heteroaryl group being optionally substituted by one or two substituents independently selected from $C_1$-$C_2$ alkyl, $C_1$-$C_2$ alkoxy and $C_1$-$C_2$ haloalkoxy.

In yet another embodiment, $R^3$ represents a 6-membered monocyclic heteroaromatic group containing one or two ring nitrogen atoms, the heteroaromatic group being optionally substituted by one, two, three or four substituents independently selected from fluorine, chlorine, bromine, $C_1$, $C_2$ or $C_3$ alkyl, $C_1$, $C_2$ or $C_3$ haloalkyl, $C_1$, $C_2$ or $C_3$ alkoxy, $C_1$, $C_2$ or $C_3$ haloalkoxy, —$NR^{10}R^{11}$ or a 5- to 6-membered heteroaryl group which is unsubstituted.

In a still further embodiment, $R^3$ represents any one of the following moieties or is selected from a group containing two or more of such moieties in any combination:

(i) 3-chloropyridin-2-yl,
(ii) 3-bromopyridin-2-yl,
(iii) 3-methoxypyridin-2-yl,
(iv) 3-(propan-2-yloxy)pyridin-2-yl,
(v) 6-bromo-3-methoxypyridin-2-yl,
(vi) 3-(1H-pyrazol-1-yl)pyridin-2-yl,
(vii) 3-fluoropyridin-2-yl,
(viii) 3-(piperidin-1-yl)pyridin-2-yl,
(ix) 3-(azetidin-1-yl)pyridin-2-yl,
(x) 3-(pyrrolidin-1-yl)pyridin-2-yl,
(xi) 3-(3-methoxyazetidin-1-yl)pyridin-2-yl,
(xii) 3-methoxy-6-(trifluoromethyl)pyridin-2-yl,
(xiii) 3-ethoxypyridin-2-yl,
(xiv) 3-(trifluoromethoxy)pyridin-2-yl,
(xv) 3-(difluoromethoxy)pyridin-2-yl,
(xvi) 3-(1H-1,2,3-triazol-1-yl)pyridin-2-yl,
(xvii) 3-ethoxy-6-methylpyridin-2-yl,
(xviii) 3-methoxy-6-methylpyridin-2-yl, and
(xix) 3-(2H-1,2,3-triazol-2-yl)pyridin-2-yl.

In a still further embodiment, when $R^3$ represents a substituted 5- or 6-membered monocyclic heteroaromatic group, the substituent(s) is/are independently any one of the following moieties or is/are independently selected from a group containing two or more of such moieties in any combination:
(i) methyl,
(ii) trifluoromethyl,
(iii) methoxy,
(iv) ethoxy,
(v) isopropyloxy,
(vi) difluoromethoxy,
(vii) trifluoromethoxy,
(viii) fluorine,
(ix) chlorine,
(x) bromine,
(xi) triazolyl (e.g. 1,2,3-triazol-2-yl, 1,2,3-triazol-1-yl or 1,2,4-triazol-1-yl),
(xii) pyrazolyl (e.g. pyrazol-1-yl),
(xiii) oxadiazolyl,
(xiv) 3-methyl-1,2,4-oxadiazol-5-yl,
(xv) azetidinyl (e.g. azetidin-1-yl),
(xvi) 3-methoxyazetidin-1-yl,
(xvii) pyrrolidinyl (e.g. pyrrolidin-1-yl),
(xviii) piperidinyl (e.g. piperidin-1-yl),
(xix) pyrimidinyl (e.g. pyrimidin-2-yl),
(xx) imidazolyl (e.g. imidazol-1-yl), and
(xxi) cyclopropyl.

When $R^3$ represents a substituted 6-membered monocyclic heteroaromatic group, the substituent(s) is/are preferably attached in the ortho- and/or meta-positions relative to the point of attachment of the amide moiety, —$NR^2C(O)$—.

$R^4$ and $R^5$ each independently represent a hydrogen atom or a $C_1$, $C_2$ or $C_3$ alkyl or $C_3$-$C_6$ cycloalkyl (cyclopropyl, cyclobutyl, cyclopentyl or cyclohexyl) group, or $R^4$ and $R^5$ may together with the nitrogen atom to which they are attached form a 4-, 5-, 6- or 7-membered saturated heterocyclic ring optionally substituted by at least one substituent, e.g. one or two substituents, independently selected from halogen (e.g. fluorine, chlorine, bromine or iodine), hydroxyl and $C_1$, $C_2$ or $C_3$ alkoxy.

In one aspect, the saturated heterocyclic ring may contain a single ring heteroatom (being the nitrogen atom to which $R^4$ and $R^5$ are attached).

In an alternative aspect, the saturated heterocyclic ring may contain a second ring heteroatom selected from a nitrogen or oxygen atom.

In one embodiment, $R^4$ and $R^5$ each independently represent a hydrogen atom or a $C_1$, $C_2$ or $C_3$ alkyl or $C_3$-$C_6$ or $C_3$-$C_5$ or $C_5$-$C_6$ cycloalkyl, particularly cyclopropyl, group, or $R^4$ and $R^5$ may together with the nitrogen atom to which they are attached form a 4- or 5-membered saturated heterocyclic ring optionally substituted by one or two substituents independently selected from fluorine, chlorine, bromine, hydroxyl and methoxy.

In a second embodiment, $R^4$ and $R^5$ each represent a hydrogen atom.

In a third embodiment, $R^4$ and $R^5$ each represent a $C_1$-$C_3$ alkyl group.

In a fourth embodiment, one of $R^4$ and $R^5$ represents a hydrogen atom and the other of $R^4$ and $R^5$ represents a $C_1$-$C_3$ alkyl group.

In a fifth embodiment, one of $R^4$ and $R^5$ represents a cyclopropyl group and the other of $R^4$ and $R^5$ represents a $C_1$-$C_3$ alkyl group.

In a sixth embodiment, $R^4$ and $R^5$ together with the nitrogen atom to which they are attached form an azetidinyl or pyrrolidinyl ring, each optionally substituted by one or two substituents independently selected from fluorine, hydroxyl and methoxy.

In a seventh embodiment, $R^4$ and $R^5$ together with the nitrogen atom to which they are attached form an azetidinyl, pyrrolidinyl or piperidinyl ring, each optionally substituted by a methoxy group.

$R^6$ and $R^7$ each independently represent a hydrogen atom or a $C_1$, $C_2$ or $C_3$ alkyl or $C_3$-$C_6$ cycloalkyl (cyclopropyl, cyclobutyl, cyclopentyl or cyclohexyl) group, or $R^6$ and $R^7$ may together with the nitrogen atom to which they are attached form a 4-, 5-, 6- or 7-membered saturated heterocyclic ring optionally substituted by at least one substituent, e.g. one or two substituents, independently selected from halogen (e.g. fluorine, chlorine, bromine or iodine) and hydroxyl.

In one aspect, the saturated heterocyclic ring may contain a single ring heteroatom being the nitrogen atom which $R^6$ and $R^7$ are attached).

In an alternative aspect, the saturated heterocyclic ring may contain a second ring heteroatom selected from a nitrogen or oxygen atom.

In one embodiment, $R^6$ and $R^7$ each independently represent a hydrogen atom or a $C_1$, $C_2$ or $C_3$ alkyl or $C_3$-$C_6$ or $C_3$-$C_5$ or $C_5$-$C_6$ cycloalkyl, particularly cyclopropyl, and group, or $R^6$ and $R^7$ may together with the nitrogen atom to which they are attached form a 4 or 5-membered saturated heterocyclic ring optionally substituted by one or two substituents independently selected from fluorine, chlorine, bromine and hydroxyl.

In a second embodiment, $R^6$ and $R^7$ each represent a hydrogen atom.

In a third embodiment, $R^6$ and $R^7$ each represent a $C_1$-$C_3$ alkyl group.

In a fourth embodiment, one of $R^6$ and $R^7$ represents a hydrogen atom and the other of $R^6$ and $R^7$ represents a $C_1$-$C_3$ alkyl group.

In a fifth embodiment, one of $R^6$ and $R^7$ represents a cyclopropyl group and the other of $R^6$ and $R^7$ represents a $C_1$-$C_3$ alkyl group.

In a sixth embodiment, $R^6$ and $R^7$ together with the nitrogen atom to which they are attached form an azetidinyl or pyrrolidinyl ring optionally substituted by one or two substituents independently selected from fluorine and hydroxyl.

$R^9$ represents a $C_1$-$C_6$, or $C_1$-$C_4$, or $C_1$-$C_2$ alkyl, $C_1$-$C_6$, or $C_1$-$C_4$, or $C_1$-$C_2$ alkoxy, benzyloxy, $C_6$-$C_{10}$ aryl, or heteroaryl group.

In one embodiment, $R^9$ represents a $C_1$-$C_2$ alkyl, $C_1$-$C_2$ alkoxy or benzyloxy group.

In another embodiment, $R^9$ represents a $C_1$-$C_2$ alkoxy or benzyloxy group.

$R^{10}$ and $R^{11}$ are defined as for $R^4$ and $R^5$ above.
$R^{12}$ and $R^{13}$ are defined as for $R^6$ and $R^7$ above.

In a preferred embodiment of the invention,
$R^1$ represents a 9- or 10-membered fused bicyclic heteroaromatic group optionally substituted by at least one halogen atom;
L represents NH;
$R^a$ represents a hydrogen atom;
$R^b$ represents a hydrogen atom;
X represents $CHR^8$;
$R^2$ represents hydrogen or methyl;
$R^3$ represents a 5- or 6-membered monocyclic heteroaromatic group optionally substituted by at least one substituent independently selected from fluorine, chlorine, bromine, $C_1$-$C_3$ alkyl, $C_1$-$C_3$ alkoxy, or a 5- or 6-membered heteroaryl group; and
$R^8$ represents a hydrogen atom.

In another preferred embodiment,
$R^1$ represents a 9- or 10-membered fused bicyclic heteroaromatic group optionally substituted by at least one halogen atom;
L represents NH;
$R^a$ represents a hydrogen atom;
$R^b$ represents a hydrogen atom;
X represents $CHR^8$;
$R^2$ represents hydrogen or methyl;
$R^3$ represents a pyridinyl group optionally substituted by at least one substituent, e.g. one or two substituents, independently selected from fluorine, chlorine, bromine, $C_1$-$C_3$ alkyl, $C_1$-$C_3$ haloalkyl, $C_1$-$C_3$ alkoxy, $C_1$-$C_3$ haloalkoxy, —$NR^{10}R^{11}$ or a 5- to 6-membered heteroaryl group which is unsubstituted;
$R^8$ represents a hydrogen atom; and
$R^{10}$ and $R^{11}$ together with the nitrogen atom to which they are attached form a 4- to 6-membered saturated heterocyclic ring optionally substituted by at least one $C_1$-$C_3$ alkoxy group.

Examples of compounds of the invention include:
3-Bromo-N-[(1S,2S)-2-[(6-fluoro-1,3-benzothiazol-2-yl)amino]cyclopentyl]-pyridine-2-carboxamide;
6-Bromo-N-[(1S,2S)-2-[(6-fluoro-1,3-benzothiazol-2-yl)amino]cyclopentyl]-3-methoxypyridine-2-carboxamide;
N-[(1S,2S)-2-[(6-Fluoro-1,3-benzothiazol-2-yl)amino]cyclopentyl]-3-methoxypyridine-2-carboxamide;
3-Chloro-N-[(1S,2S)-2-[(6-fluoro-1,3-benzothiazol-amino]cyclopentyl]pyridine-2-carboxamide;
N-[(1S,2S)-2-[(6-Fluoro-1,3-benzothiazol-2-yl)amino]cyclopentyl]-3-methoxy-N-methylpyridine-2-carboxamide;
N-[(1S,2S)-2-[(6-Fluoro-1,3-benzothiazol-2-yl)amino]cyclopentyl]-3-(2H-1,2,3-triazol-2-yl)pyridine-2-carboxamide;
N-[(1S,2S)-2-[(6-Fluoro-1,3-benzoxazol-2-yl)amino]cyclopentyl]-3-methoxypyridine-2-carboxamide;
N-[(1S,2S)-2-[(6-Fluoro-1,3-benzothiazol-2-yl)amino]cyclopentyl]-3-(propan-2-yloxy)pyridine-2-carboxamide;
N-[(1S,2S)-2-[(6-Fluoro-1,3-benzothiazol-2-yl)amino]cyclopentyl]-3-methoxy-6-methylpyridine-2-carboxamide;
N-[(1S,2S)-2-[(6-fluoro-1,3-benzothiazol-2-yl)amino]cyclopentyl]-3-(1H-pyrazol-1-yl)pyridine-2-carboxamide;
3-Fluoro-N-[(1S,2S)-2-[(6-fluoro-1,3-benzothiazol-2-yl)amino]cyclopentyl]pyridine-2-carboxamide;
N-[(1S,2S)-2-[(6-Fluoro-1,3-benzothiazol-2-yl)amino]cyclopentyl]-3-(piperidin-1-yl)pyridine-2-carboxamide;
3-(Azetidin-1-yl)-N-[(1S,2S)-2-[(6-fluoro-1,3-benzothiazol-2-yl)amino]cyclopentyl]pyridine-2-carboxamide;
N-[(1S,2S)-2-[(6-Fluoro-1,3-benzothiazol-2-yl)amino]cyclopentyl]-3-(pyrrolidin-1-yl)pyridine-2-carboxamide;
N-[(1S,2S)-2-[(6-Fluoro-1,3-benzothiazol-2-yl)amino]cyclopentyl]-3-(3-methoxyazetidin-1-yl)pyridine-2-carboxamide;
3-Methoxy-N-[(1S,2S)-2-[(quinoxalin-2-yl)amino]cyclopentyl]pyridine-2-carboxamide;
N-[(1S,2S)-2-[(6-Fluoro-1,3-benzothiazol-2-yl)amino]cyclopentyl]-3-methoxy-6-(trifluoromethyl)pyridine-2-carboxamide;
3-Ethoxy-N-[(1S,2S)-2-[(6-fluoro-1,3-benzothiazol-2-yl)amino]cyclopentyl]pyridine-2-carboxamide;
N-[(1S,2S)-2-[(6-fluoro-1,3-benzothiazol-2-yl)amino]cyclopentyl]-3-(trifluoromethoxy)pyridine-2-carboxamide;
3-(Difluoromethoxy)-N-[(1S,2S)-2-[(6-fluoro-1,3-benzothiazol-2-yl)amino]cyclopentyl]pyridine-2-carboxamide;
N-[(1S,2S)-2-[(6-Chloro-1,3-benzothiazol-2-yl)amino]cyclopentyl]-3-(2H-1,2,3-triazol-2-yl)pyridine-2-carboxamide;
N-[(1S,2S)-2-[(6-Chloro-1,3-benzothiazol-2-yl)amino]cyclopentyl]-3-(difluoromethoxy)pyridine-2-carboxamide;
3-(Difluoromethoxy)-N-[(1S,2S)-2-[(6-fluoro-1,3-benzoxazol-2-yl)amino]cyclopentyl]pyridine-2-carboxamide;
N-[(1S,2S)-2-[(6-Fluoro-1,3-benzothiazol-2-yl)amino]cyclopentyl]-3-(1H-1,2,3-triazol-1-yl)pyridine-2-carboxamide;
N-[(1S,2S)-2-[(6-Chloro-1,3-benzoxazol-2-yl)amino]cyclopentyl]-3-(difluoromethoxy)pyridine-2-carboxamide;
3-Ethoxy-6-methyl-N-[2-(quinolin-2-ylmethyl)cyclopentyl]pyridine-2-carboxamide;
3-Ethoxy-6-methyl-N-[2-(quinolin-2-ylmethyl)cyclopentyl]pyridine-2-carboxamide;
enantiomers thereof and pharmaceutically acceptable salts of any of the foregoing.

It should be noted that each of the chemical compounds listed above represents a particular and independent aspect of the invention.

The present invention further provides a process for the preparation of a compound of formula (I) or a pharmaceutically acceptable salt thereof as defined above which comprises
(i) reacting a compound of formula

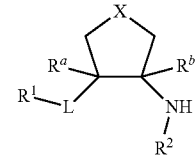

(II)

wherein L, X, $R^a$, $R^b$, $R^1$ and $R^2$ are as defined in formula (I), with a compound of formula

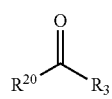

(III)

wherein $R^{20}$ represents a halogen atom (e.g. chlorine atom) or a hydroxyl group and $R^3$ is as defined in formula (I), or a salt (e.g. hydrochloride salt) thereof; or (ii) when L represents NH or N(CH$_3$), reacting a compound of formula (IV)

$$R^{25}-NH \quad \begin{array}{c} X \\ R^a \bigg\langle \bigg\rangle R^b \\ N-R^3 \\ | \quad \| \\ R^2 \quad O \end{array}$$

wherein $R^{25}$ represents a hydrogen atom or methyl group and X, $R^a$, $R^b$, $R^2$ and $R^3$ are as defined in formula (I), with a compound of formula (V), $R^1$-LG$^1$, wherein LG$^1$ represents a leaving group (e.g. a halogen atom) and $R^1$ is as defined in formula (I);

and optionally thereafter carrying out one or more of the following procedures:
  converting a compound of formula (I) into another compound of formula (I)
  removing any protecting groups
  forming a pharmaceutically acceptable salt.

Process (i) may conveniently be carried out by combining the amine of formula (II) with an acid chloride of formula (III) in the presence of a base such as triethyl amine or DIPEA (N,N-diisopropylethylamine) in a solvent such as dichloromethane. Alternatively the reaction can be carried out from the amine of formula (II) and a carboxylic acid of formula (III) using any of the known coupling reagents such as EDC (1-ethyl-3-(3-dimethylaminopropyl)carbodiimide) and HOAt (7-aza-1-hydroxybenzotriazole), with or HATU (1[bis(dimethylamino)methylene]-1H-1,2,3-triazolo[4,5-b]pyridinium 3-oxid hexafluorophosphate) with a base such as DIPEA. Another method is to activate the carboxylic acid to the corresponding acid chloride in situ for example with oxalyl chloride in the presence of a catalytic amount of DMF.

Process (ii) may conveniently be carried out by mixing the compound of formula (IV) with the compound of formula (V) in a solvent such as DMSO, acetonitrile or toluene and optionally in the presence of a base such as DIPEA, and heating conventionally or using microwave irradiation.

Compounds of formula (II) in which L represents CH$_2$, X represents CH$_2$ and $R^a$ and $R^b$ are each hydrogen may be prepared according to the scheme below. The heterocyclic bromomethylene compound is likely to be commercially available or can be prepared by bromination of the corresponding heterocyclic methyl compound using, for example, N-bromosuccinimide and benzoyl peroxide in carbon tetrachloride at elevated temperature. Reaction of the heterocyclic bromomethylene compound with triphenylphosphine in toluene at raised temperature will afford the corresponding phosphonium bromide which on treatment with a base such as n-butyl lithium in the presence of the Boc-protected cyclic ketone will afford the corresponding alkene. The alkene can be reduced by hydrogenation using hydrogen gas in the presence of a catalyst such as palladium on carbon. Finally, the Boc protecting group can be removed using methods known to those skilled in the art, e.g. acid hydrolysis.

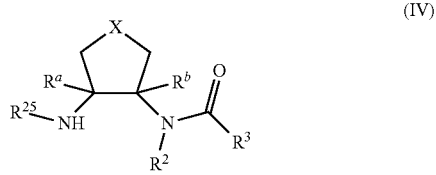

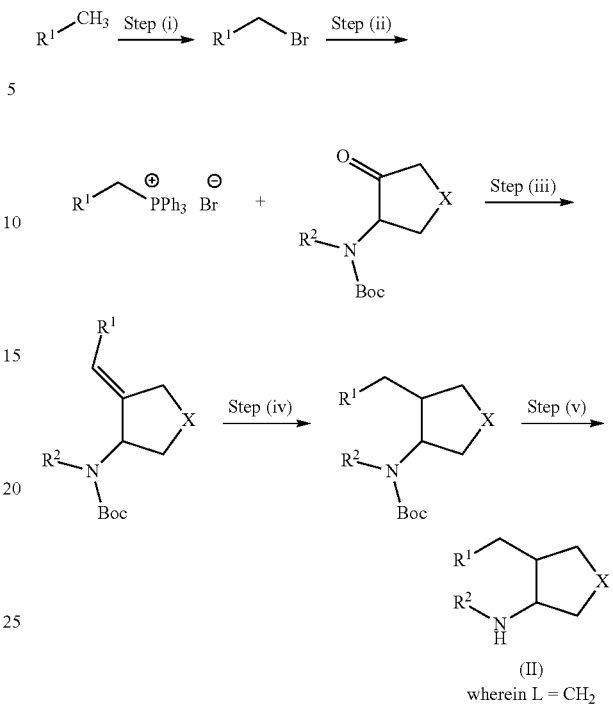

wherein L = CH$_2$

Boc = tert-butyloxycarbonyl

Compounds of formula (II) in which L represents an oxygen atom may be prepared by reacting a compound of formula (VI)

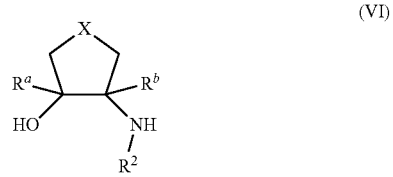

wherein X, $R^a$, $R^b$ and $R^2$ is as defined in formula (II), with a compound of formula (V) as defined above, in the presence of a base such as sodium hydride.

Compounds of formula (IT) in which L represents NH or N(CH$_3$) may be prepared by reacting a compound of formula (VII)

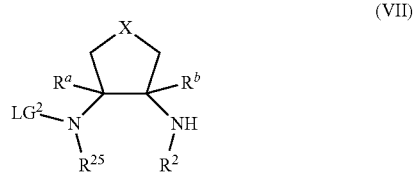

in which LG$^2$ represents a protecting group such as a tert-butyloxycarbonyl group, and X, $R^a$, $R^b$, $R^2$ and $R^{25}$ are as defined in formula (IV) above, with a compound of formula (V) as defined above.

Compounds of formula (II) in which X represents NC(O)R⁹ may be prepared by acylating a compound of formula

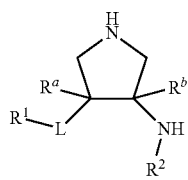

(VIII)

in which L, R$^a$, R$^b$, R$^1$ and R$^2$ are as defined in formula (II), with an acylating agent of formula (IX), R⁹C(O)-LG³, in which LG³ represents a leaving group (e.g. a halogen atom) and R is as defined in formula (I).

Compounds of formula (IV) may be prepared by reacting a compound of formula (VII) with a compound of formula (III) followed by removal of the protecting group, LG², by acid treatment using, for example, an acid such as hydrochloric acid.

Compounds of formula (IV) in which X represents NC(O)R⁹ may be prepared by acylating a compound of formula

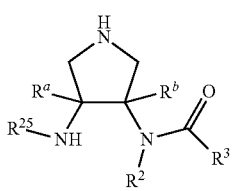

(X)

in which R$^a$, R$^b$, R$^2$, R$^3$ and R$^{25}$ are as defined in formula (IV), with an acylating agent of formula (IX) as defined above.

Compounds of formulae (III), (V), (VI), (VII), (VIII), (IX) and (X) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley—Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1$H, $^2$H and $^3$H. Similarly carbon atoms are to be understood to include $^{12}$C, $^{13}$C and $^{14}$C, nitrogen atoms are to be understood to include $^{14}$N and $^{15}$N, and oxygen atoms are to be understood to include $^{16}$O, $^{17}$O and $^{18}$O.

In a further aspect of the invention, compounds of formula may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as orexin receptor antagonists, and may be used in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease).

Thus, the present invention provides a compound of formula (I) or a pharmaceutically acceptable salt thereof as hereinbefore defined for use in therapy, in particular for the treatment of conditions whose development or symptoms are linked to orexin receptor activity.

The present invention also provides the use of a compound of formula (I) or a pharmaceutically acceptable salt thereof as hereinbefore defined for the preparation of a medicament for the treatment of conditions whose development or symptoms are linked to orexin receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), anxiety disorders (such as post-traumatic stress disorder or panic disorders), or addiction.

The invention also provides a method of treating at least one symptom or condition associated with schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% of active ingredient, all percentages by weight being based on total composition.

The compounds of the invention (that is, compounds of formula and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipratnine, venlafaxine, vortioxetine and equivalents and pharmaceutically active isomer(s) and/or metabolite(s) thereof;

(ii) antipsychotics including, for example, amisulpride, aripiprazole, asenapine, benzisoxidil, bifeprunox, brexpiprazole, carbamazepine, cariprazine, clozapine, chlorpromazine, debenzapine, divalproex, duloxetine, eszopiclone, haloperidol, iloperidone, lamotrigine, loxapine, lurasidone, mesoridazine, olanzapine, paliperidone, perlapine, perphenazine, phenothiazine, phenylbutlypiperidine, pimozide, prochlorperazine, quetiapine, risperidone, sertindole, sulpiride, suproclone, suriclone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, valproate, lamotrigine, levetiracetam and gabapentin, and equivalents and pharmaceutically active isomer(s) and/or metabolite(s) thereof;

(v) Alzheimer's therapies including, for example, donepezil, galantamine, memantine, rivastigmine, tacrine, and equivalents and pharmaceutically active isomer(s) and/or metabolite(s) thereof;

(vi) Parkinson's therapies including, for example, L-dopa, ropinirole, pramipexole, monoamine oxidase type B (MAO-B) inhibitors such as deprenyl, selegiline and rasagiline, catechol-O-methyl transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(vii) migraine therapies including, for example, almotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zomitriptan, and equivalents and pharmaceutically active isomer(s) and/or metabolite(s) thereof;

(viii) stroke therapies including, for example, abciximab, activase, citicoline, desmoteplase, and equivalents and pharmaceutically active isomer(s) and/or metabolite(s) thereof;

(ix) urinary incontinence therapies including, for example, darafenacin, duloxetine, falvoxate, mirabegron, oxybutynin, propiverine, robalzotan, solifenacin, and tolterodine, and equivalents and pharmaceutically active isomer(s) and/or metabolite(s) thereof;

(x) neuropathic pain therapies including, for example, capsaicin, gabapentin, lidoderm, and pregabalin, and equivalents and pharmaceutically active isomer(s) and/or metabolite(s) thereof;

(xi) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, lorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and zolpidem, zopiclone and equivalents and pharmaceutically active isomer(s) and/or metabolite(s) thereof;

(xiii) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xiv) 5HT1B ligands such as, for example, compounds disclosed in WO 99/05134 and WO 02/08212;

(xv) mGluR2 agonists;

(xvi) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xvii) chemokine receptor CCR1 inhibitors; and (xviii) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts ($\delta$) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative High Performance Liquid Chromatography (HPLC) was performed using an Agilent Technologies 1100 Series system or Waters autopurification system typically using Waters 19 mm id×100 mm or 19 mm id×250 mm C18 columns such as XBridge or SunFire 5 μm materials at 20 mL/min. Mobile phases typically consisted of acetonitrile or methanol mixed with water containing either 0.1% formic acid or 0.1% ammonia, unless stated otherwise.

In the following descriptions "room temperature" denotes a temperature in the range from 20° C. to 25° C.

The abbreviations used in the specific examples have the following meanings:

Aza-HOBt (HOAt)=7-Aza-1-hydroxybenzoniazole
Boc=tert-Butyloxycarbonyl
DCM=Dichloromethane
DIPEA=N,N-Diisopropylethylamine
DMF=N,N-Dimethylformamide
DMSO=Dimethyl sulfoxide
EDC=1-Ethyl-3-(3-dimethylaminopropyl)carbodiimide
HATU=1-[Bis(dimethylamino)methylene]-1H-1,2,3-triazolo[4,5-b]pyridinium 3-oxid hexafluorophosphate
Herrmanns Catalyst=trans-bis(Acetato)bis[o-(di-o-tolylphosphino)benzyl] dipalladium(II)
RuPhos-Palladacycle=Chloro(2-dicyclohexylphosphino-2',6'-di-i-propoxy-1,1'-biphenyl)[2-(2-aminoethylphenyl)] palladium(II), methyl-t-butylether adduct
TBTU=O-(Benzotriazol-1-yl)-N,N,N',N'-tetramethyluronium tetrafluoroborate
THF=Tetrahydrofuran

1. INTERMEDIATES

Intermediate 1: (1S,2S)-1-N-(6-Fluoro-1,3-benzothiazol-2-yl)cyclopentane-1,2-diamine hydrochloride

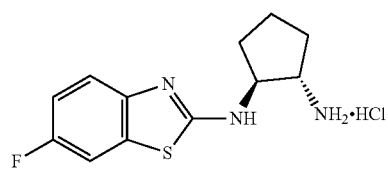

A microwave vial was charged with tert-butyl N-[(1S, 2S)-2-aminocyclopentyl]carbamate (CAS number 586961-34-4; 1.00 g, 4.99 mmol) and 2-chloro-6-fluoro-1,3-benzothiazole (CAS number 399-74-6; 1.03 g, 5.49 mmol) in dry DMSO (15 ml). DIPEA (2.62 ml, 14.98 mmol) was added, the vial flushed with nitrogen and sealed. The reaction mixture was subjected to microwave irradiation at 140° C. for 1.5 hours and upon cooling was dissolved in ethyl acetate and washed with HCl (0.5 M), water and brine. The organics were filtered through a hydrophobic frit and concentrated in mow. The crude material was purified by column chromatography (silica, 0-50% ethyl acetate/petrol) to afford the Boc-protected intermediate which was dissolved in 1,4-dioxane (5 ml) and then HCl in 1,4-dioxane (4 M, 4 ml, 16.00 mmol) was added. The reaction was stirred at room temperature for 2 hours and concentrated in vacuo to afford the title compound.

MS ES+: 252

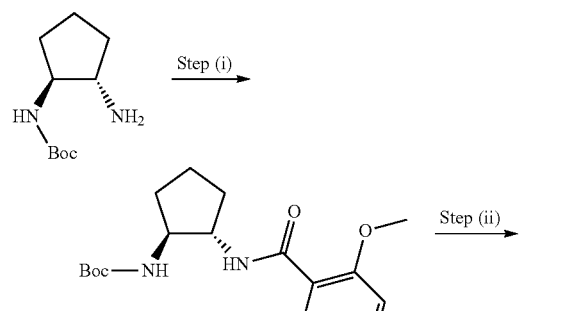

Intermediate 2: N-[(1S,2S)-2-Aminocyclopentyl]-3-methoxypyridine-2-carboxamide hydrochloride

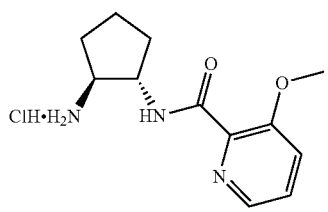

Step (i): tert-Butyl N-[(1S,2S)-2-(3-methoxypyridine-2-amido)cyclopentyl]carbamate A solution of 3-methoxypyridine-2-carboxylic acid (CAS number 16478-52-7; 0.84 g, 5.49 mmol), tert-butyl N-[(1S, 2S)-2-aminocyclopentyl]carbamate (CAS number 586961-34-4; 1.00 g, 4.99 mmol), HATU (2.85 g, 7.49 mmol) and triethylamine (2.09 ml, 14.98 mmol) in dry DMF (16.6 ml) was stirred at room temperature for 17 hours. The reaction mixture was partitioned between ethyl acetate and water. The organics were washed with water and brine, dried over magnesium sulfate, filtered and concentrated in mow. The crude product was purified by column chromatography (silica, 0-100% ethyl acetate/petrol then 0-30% methanol/ethyl acetate to afford the title compound.

MS ES+: 336

Step (ii): N-[(1S,2S)-2-Aminocyclopentyl]-3-methoxypyridine-2-carboxamide hydrochloride tert-Butyl N-[(1S,2S)-2-(3-methoxypyridine-2-amido)cyclopentyl]carbamate (880 mg, 2.62 mmol) was dissolved in HCl in 1,4-dioxane (4 M, 10 ml, 40.0 mmol) and the reaction was stirred at room temperature for 3 hours. The reaction mixture was filtered and the resultant solid was sonicated in ethyl acetate/methanol (10:1) and then filtered again. Drying afforded the first batch of the title compound. The mother liquors from both filtrations were combined, concentrated and azeotropically distilled with toluene followed by acetonitrile. The solvent was evaporated in vacuo to afford a second batch of the title compound.

$^1$H NMR (DMSO-$d_6$) δ ppm 1.59-1.79 (m, 4H), 2.01-2.14 (m, 2H), 3.43-3.51 (m, 1H), 3.90 (s, 3H), 4.15-4.30 (m, 1H), 7.62-7.68 (m, 1H), 7.76-7.83 (m, 1H), 8.21-8.36 (m, 3H), 8.71-8.78 (m, 1H)

MS ES+: 236

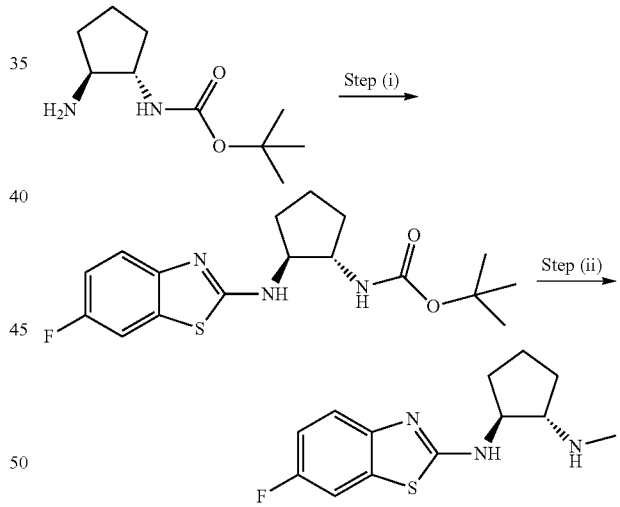

Intermediate 3: (1S,2S)-1-N-(6-Fluoro-1,3-benzothiazol-2-yl)-2-N-methyl-cyclopentane-1,2-diamine

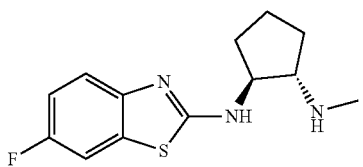 [SMILES: CN[C@H]1CCC[C@@H]1Nc1nc2ccc(F)cc2s1]

Step (i): tert-Butyl N-[(1S,2S)-2-[(6-fluoro-1,3-benzothiazol-2-yl)amino]cyclopentyl]-carbamate A microwave vial was charged with tert-butyl N-[(1S,2S)-2-aminocyclopentyl]carbamate (CAS number 586961-34-4; 1.00 g, 4.99 mmol) and 2-chloro-6-fluoro-1,3-benzothiazole (CAS number 399-74-6; 1.03 g, 5.49 mmol) in dry DMSO (16 ml). DIPEA (2.62 ml, 14.98 mmol) was added, the vial flushed with nitrogen and sealed. The reaction mixture was subjected to microwave irradiation at 140° C. for 1.5 hours then partitioned between ethyl acetate and water. The organics were washed with brine, filtered through a hydrophobic frit and concentrated in vacuo. The crude material was purified by column chromatography (silica, 0-50% ethyl acetate/diethyl ether) to afford the title compound.

MS ES+: 352

Step (ii): (1S,2S)-1-N-(6-Fluoro-1,3-benzothiazol-2-yl)-2-N-methyl-cyclopentane-1,2-diamine tert-Butyl N-[(1S,2S)-2-[(6-fluoro-1,3-benzothiazol-2-yl)amino]cyclopentyl]-carbamate (150 mg, 0.43 mmol) was dissolved in dry THF (1.4 ml). To this was added drop wise a solution of lithium aluminium hydride in THF (1 M, 0.64 ml, 0.64 mmol) and the reaction mixture heated at 60° C. for 3 hours. The reaction was quenched by the addition of sodium sulfate decahydrate and filtered. The organics were concentrated in vacuo and the crude material purified by column chromatography (basic silica, 0-100% ethyl acetate/petrol then 0-20% methanol/ethyl acetate) to afford the title compound.

MS ES+: 266

Intermediate 4:
2-Chloro-3-methoxy-6-(trifluoromethyl)pyridine

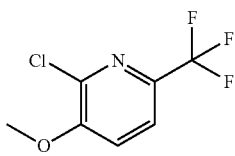

To a solution of 2-chloro-6-(trifluoromethyl)pyridin-3-ol (CAS number 731002-60-1; 1.00 g, 5.06 mmol) in dry DMF (10 ml) was added potassium carbonate (0.84 g, 6.07 mmol) and methyl iodide (0.38 ml, 6.07 mmol). The reaction was stirred at room temperature for 72 hours then partitioned between ethyl acetate and water. The organics were washed with water and brine, filtered through a hydrophobic frit and concentrated in vacuo. The crude material was purified by column chromatography (silica, 0-100% ethyl acetate/petrol, then 0-20% methanol/ethyl acetate) to afford the title compound.

$^1$H NMR (400 MHz, DMSO-d$_6$) δ ppm 4.00 (s, 3H), 7.74-7.83 (m, 1H), 7.91-8.01 (m, 1H)

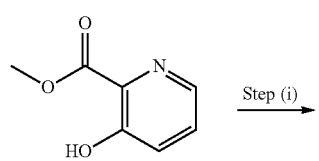

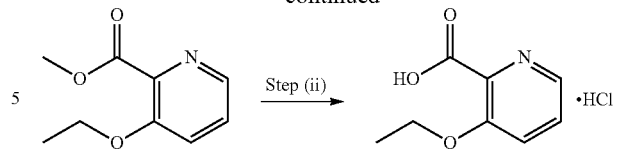

Intermediate 5: 3-Ethoxypyridine-2-carboxylic acid hydrochloride

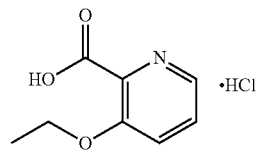

Step (i): Methyl 3-ethoxypyridine-2-carboxylate

To a solution of methyl 3-hydroxypyridine-2-carboxylate (CAS number 62733-99-7; 1.00 g, 6.53 mmol) in dry DMF (22 ml) was added potassium carbonate (1.08 g, 7.84 mmol) and iodoethane (1.22 g, 7.84 mmol). The reaction mixture was stirred at room temperature for 72 hours then partitioned between ethyl acetate and water. The organics were washed with water, filtered through a hydrophobic frit and concentrated in vacuo to afford the title compound.

$^1$H NMR (400 MHz, DMSO-d$_6$) δ ppm 1.32 (t, J=7.07 Hz, 3H), 3.84 (s, 3H), 4.14 (q, J=7.07 Hz, 2H), 7.47-7.56 (m, 1H), 7.60-7.67 (m, 1H), 8.12-8.20 (m, 1H)

Step (ii): 3-Ethoxypyridine-2-carboxylic acid

A solution of methyl 3-ethoxypyridine-2-carboxylate (1.18 g, 6.53 mmol) and NaOH (2 M, 16.3 ml, 32.6 mmol) in THF (22 ml) was stirred at room temperature for 17 hours. The reaction mixture was concentrated in vacuo and the residue partitioned between ethyl acetate and water. The aqueous layer was acidified to pH 5 and extracted with ethyl acetate, the product remained in the aqueous which was concentrated in vacuo to afford the title compound.

$^1$H NMR (300 MHz, DMSO-d$_5$) δ ppm 1.21-1.34 (m, 3H), 3.91-4.06 (m, 2H), 6.98-7.11 (m, 1H), 7.16-7.28 (m, 1H), 7.82-7.94 (m, 1H)

MS ES+: 168

Intermediate 6: Methyl 3-(difluoromethoxy)pyridine-2-carboxylate

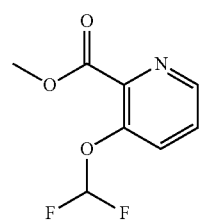

To a solution of methyl 3-hydroxypyridine-2-carboxylate (CAS number 62733-99-7; 500 mg, 3.27 mmol) in dry DMF (11 ml) was added 2-chloro-2,2-difluoroacetic acid, sodium (802 mg, 5.22 mmol) and potassium carbonate (812 mg, 5.88 mmol). The reaction mixture was sealed and stirred at 70° C. for 17 hours then partitioned between ethyl acetate and water. The organics were washed with water and brine, filtered through a hydrophobic frit and concentrated in vacuo. The crude material was purified by column chromatography (silica, 0-100% ethyl acetate/petrol) to afford the title compound.

MS ES+: 204

Intermediate 7:
3-(Difluoromethoxy)pyridine-2-carboxylic acid sodium

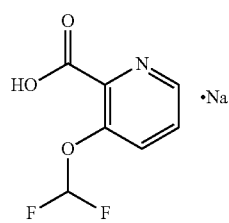

To a solution of methyl 3-(difluoromethoxy)pyridine-2-carboxylate (intermediate 6; 200 mg, 0.99 mmol) in THF (3.2 ml) was added NaOH (2 M, 517 μl, 1.034 mmol). The reaction mixture was stirred at room temperature for 4 hours. To this was then added further NaOH (2 M, 100 μl, 0.20 mmol) and the reaction was stirred at room temperature for a further 2 hours. The reaction mixture was concentrated in vacuo and the residue partitioned between ethyl acetate and water. The aqueous layer was concentrated in vacuo to afford the title compound.

$^1$H NMR (400 MHz, DMSO-$d_6$) δ ppm 7.02-7.45 (m, 2H), 7.46-7.55 (m, 1H), 8.22-8.33 (m, 1H)

MS ES+: 190

Intermediate 8:
3-(Difluoromethoxy)pyridine-2-carboxylic acid

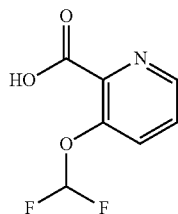 [SMILES: O=C(O)c1ncccc1OC(F)F]

To a solution of methyl 3-(difluoromethoxy)pyridine-2-carboxylate (intermediate 6; 221 mg, 1.09 mmol) in THF (1.5 ml) and water (0.2 ml) was added lithium hydroxide (78 mg, 3.26 mmol). The reaction mixture was stirred at room temperature for 2 hours then concentrated in vacuo. The residue was acidified with HCl (aq, 2M) and extracted with ethyl acetate. The organics were dried over sodium sulfate and concentrated in mow to afford the title compound.

$^1$H NMR (400 MHz, DMSO-$d_6$) δ ppm 7.06-7.50 (m, 1H), 7.59-7.69 (m, 1H, 7.77-7.88 (m, 1H), 8.44-8.56 (m, 1H)

MS ES+: 190

Intermediate 9: (1S,2S)-1-N-(6-Chloro-1,3-benzothiazol-2-yl)cyclopentane-1,2-diamine hydrochloride

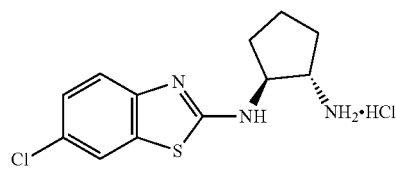

A microwave vial was charged with tert-butyl N-[(1S,2S)-2-aminocyclopentyl]carbamate (CAS number 586961-34-4; 500 mg, 2.50 mmol), 2,6-dichloro-1,3-benzothiazole (CAS number 3622-23-9; 560 mg, 2.75 mmol) and DIPEA (1308 μl, 7.49 mmol) in dry DMSO (8.3 ml). The reaction mixture was subjected to microwave irradiation at 140° C. for 2 hours then partitioned between ethyl acetate and water. The organics were washed with water and brine, dried over magnesium sulfate, filtered and concentrated in mow. The crude material was purified by column chromatography (silica, 0-100% ethyl acetate/petrol). The resultant solid was then stirred in HCl in 1,4-dioxane (4 M, 6 ml) and methanol (6 ml) at room temperature for 4 hours. The reaction mixture was concentrated in vacuo, azeotroping with toluene to afford the title compound.

$^1$H NMR (400 MHz, DMSO-$d_6$) δ ppm 1.59-1.84 (m, 4H), 2.03-2.25 (m, 2H) 3.40-3.51 (m, 1H), 4.13-4.27 (m, 1H), 7.27-7.34 (m, 1H), 7.45-7.53 (m, 1H), 7.80-7.91 (m, 1H), 8.22-8.33 (m, 2H), 8.68-8.82 (m, 1H)

MS ES+: 268

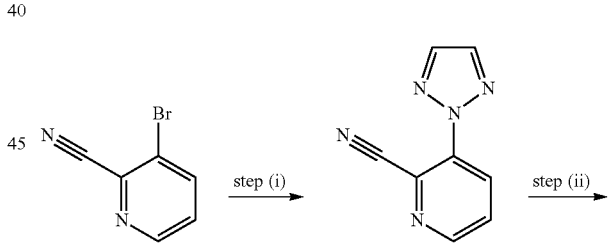

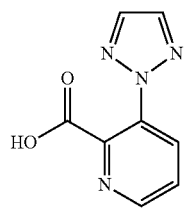 [SMILES: O=C(O)c1ncccc1-n1nccn1]

Intermediate 10: 3-(2H-1,2,3-Triazol-2-yl)pyridine-2-carboxylic acid

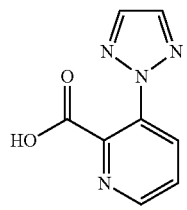

Step (i): 3-(2H-1,2,3-Triazol-2-yl)pyridine-2-carbonitrile

A microwave vial was charged with 3-bromopyridine-2-carbonitrile (CAS number 55758-02-6; 500 mg, 2.73 mmol), 2H-1,2,3-triazole (CAS number 288-36-8; 377 mg, 5.46 mmol), trans-1-N,2-N-dimethylcyclohexane-1,2-diamine (78 mg, 0.55 mmol), copper (I) trifluoromethanesulfonate benzene complex (70 mg, 0.14 mmol), cesium carbonate (1.78 g, 5.46 mmol) and DMF (5 ml). The mixture was degassed and subjected to microwave irradiation at 120° C. for 45 minutes. The reaction mixture was diluted with water and extracted with ethyl acetate. The organics were washed with water and brine, dried over sodium sulfate, filtered and concentrated in vacuo. The crude material was purified by column chromatography (silica, 0-50% ethyl acetate/petrol) to afford the title compound.

$^1$H NMR (400 MHz, DMSO-d$_6$) δ ppm 7.94-8.02 (m, 1H), 8.37 (s, 2H), 8.55-8.62 (m, 1H), 8.78-8.86 (m, 1H)

Step (ii): 3-(2H-1,2,3-Triazol-2-yl)pyridine-2-carboxylic acid

To a solution of 3-(2H-1,2,3-triazol-2-yl)pyridine-2-carbonitrile (250 mg, 1.46 mmol) ethanol (2 ml) and water (2.5 ml) was added NaOH (8 M, 0.91 ml, 7.30 mmol). The reaction mixture was heated to 100° C. for 15 hours then concentrated in vacuo to give the sodium salt of the title compound. The crude material was acidified to pH 4 with HCl (2 M) then purified by reverse phase chromatography (C18 silica, 0-100% water (with 0.1% formic acid)/acetonitrile) to afford the title compound.

$^1$H NMR (400 MHz, DMSO-d$_6$) δ ppm 7.67-7.83 (m, 1H), 8.19 (s, 2H), 8.28-8.41 (m, 1H), 8.65-8.75 (m, 1H), 13.54 (br. s., 1H)

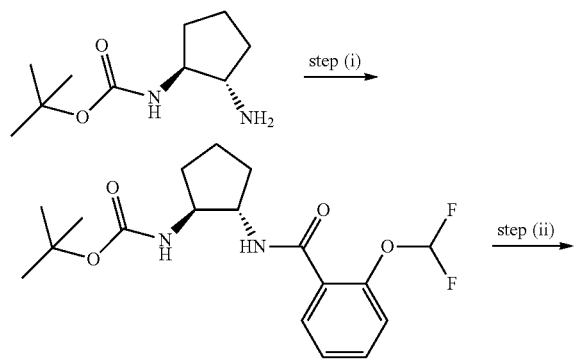

Intermediate 11: N-[(1S,2S)-2-Aminocyclopentyl]-2-(difluoromethoxy)benzamide hydrochloride

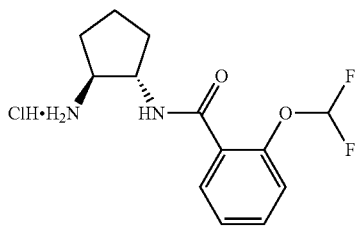

Step (i): tert-Butyl N-[(1S,2S)-2-[2-(difluoromethoxy)benzamido]-cyclopentyl]carbamate A solution of tert-butyl N-[(1S,2S)-2-aminocyclopentyl] carbamate (CAS number 586961-34-4, 150 mg, 0.75 mmol), 3-(difluoromethoxy)pyridine-2-carboxylic acid (Intermediate 8; 177 mg, 0.94 mmol), EDC (161 mg, 0.840 mmol) and 3H-[1,2,3]triazolo[4,5-b]pyridin-3-ol (101 mg, 0.750 mmol) in DMF (6 ml) was stirred at room temperature for 18 hours. The reaction mixture was diluted with ethyl acetate and washed with water, brine, dried over sodium sulfate, filtered and concentrated in vacuo. The crude product was purified by column chromatography (silica, 0-80% ethyl acetate/petrol) to afford the title compound.

$^1$H NMR (400 MHz, DCM-d$_2$) δ ppm 1.41 (s, 9H), 1.45-1.69 (m, 2H), 1.75-1.90 (m, 2H), 2.15-2.32 (m, 2H), 3.78-3.93 (m, 1H), 4.02-4.18 (m, 1H), 4.89-5.03 (m, 1H), 6.64-7.11 (m, 1H), 7.47-7.60 (m, 1H), 7.66-7.76 (m, 1H), 8.08-8.24 (m, 1H), 8.49-8.57 (m, 1H)

MS ES$^+$: 371

Step (ii): N-[(1S,2S)-2-Aminocyclopentyl]-2-(difluoromethoxy)benzamide hydrochloride A mixture of tert-butyl N-[(1S,2S)-2-[2-(difluoromethoxy)benzamido]cyclopentyl]-carbamate (221 mg, 0.60 mmol) and HCl in 1,4-dioxane (4 M, 1.5 ml, 6.00 mmol) was stirred at room temperature for 18 hours. Diethyl ether was added to the reaction mixture and the resultant solid was filtered to afford the title compound.

$^1$H NMR (400 MHz, DMSO-d$_6$) δ ppm 1.59-1.83 (m, 4H), 1.99-2.14 (m, 2H), 3.42-3.53 (m, 1H), 4.19-4.38 (m, 1H), 7.01-7.49 (m, 1H), 7.61-7.72 (m, 1H), 7.76-7.88 (m, 1H), 8.16-8.31 (m, 2H), 8.48-8.61 (m, 1H), 8.83-8.96 (m, 1H)

MS ES+: 271

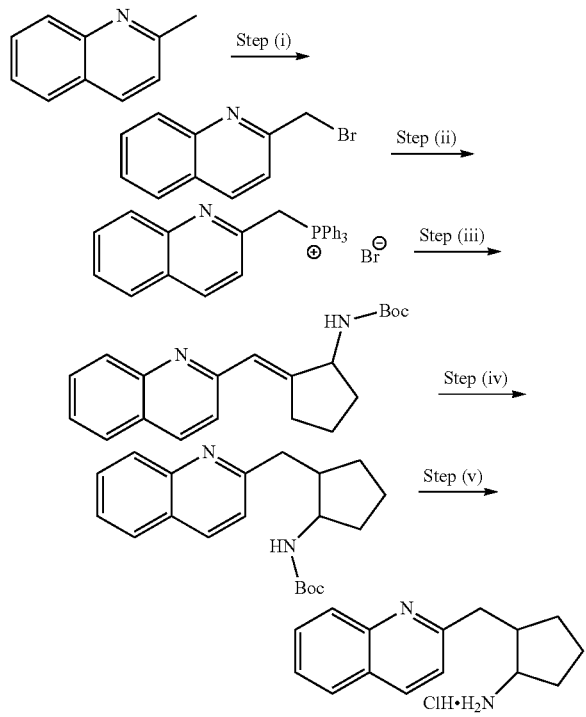

Intermediate 12:
2-(Quinolin-2-ylmethyl)cyclopentan-1-amine hydrochloride

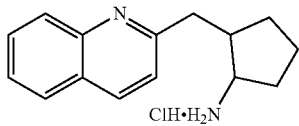

Step (i): 2-(Bromomethyl)quinoline

To a solution of 2-methylquinoline (CAS number 91-63-4; 40 g, 279 mmol) in carbon tetrachloride (700 ml) was added benzoyl peroxide (1.69 g, 6.99 mmol) and 1-bromopyrrolidine-2,5-dione (CAS number 128-08-5; 59.74 g, 335 mmol) and the resulting mixture was heated to reflux for 18 hours. The reaction mixture was filtered through diatomaceous earth (commercially sold under the trade mark "Celite"), washed with DCM and concentrated in vacuo. The crude material was purified by column chromatography (silica, 0-15% ethyl acetate/n-hexane) to afford the title compound.

$^1$H NMR (CDCl$_3$) δ ppm 4.74 (s, 2H), 7.58-7.61 (m, 2H), 7.74-7.78 (m, 1H), 7.83-7.85 (m, 1H) 8.08-8.11 (m, 1H), 8.19-8.21 (m, 1H)

Step (ii):
Triphenyl(quinolin-2-ylmethyl)phosphonium bromide

To a solution of 2-(bromomethyl)quinoline (25 g, 112 mmol) in toluene (500 ml) was added triphenylphosphine (35 g, 135 mmol) and the resulting mixture was heated to reflux for 16 hours and then concentrated in vacuo. The crude material was purified by triturating with diethyl ether to afford the title compound.

$^1$H NMR (DMSO-d$_6$) δ ppm 5.74-5.78 (m, 2H), 7.50-7.58 (m, 1H), 7.60-7.69 (m, 2H), 7.70-7.74 (m, 7H), 7.82-7.95 (m, 10H), 8.34-8.36 (m, 1H)

Step (iii): tert-Butyl N-[2-(E)-2-(quinolin-2-ylmethylidene)cyclopentyl]carbamate To a suspension of triphenyl(quinolin-2-ylmethyl)phosphonium bromide (40 g, 82.47 mmol) in THF (400 ml) was added n-butyl lithium (23%, 45.56 ml, 164.9 mmol) at 0° C. and the resulting mixture was stirred at room temperature for 2 hours. A solution of tert-butyl 2-oxocyclopentylcarbamate (CAS number 477585-30-1; 16.41 g, 82.47 mmol) in THF (50 ml) was added and the resulting mixture was stirred at room temperature for 14 hours before being quenched with a saturated solution of ammonium chloride (aq, 50 ml). The resulting mixture was then poured into water and extracted with ethyl acetate. The organics were washed with brine, dried over sodium sulfate, filtered and concentrated in vacuo. The crude product was purified by column chromatography (silica, 0-15% ethyl acetate/n-hexane) to afford the title compound.

MS ES+: 325

Step (iv): tert-Butyl
N-[2-(quinolin-2-ylmethyl)cyclopentyl]carbamate

To a solution of tert-butyl N-[2-(E)-2-(quinolin-2-ylmethylidene)cyclopentyl]carbamate (15 g, 46.3 mmol) in methanol (60 ml) was added palladium on carbon (2.0 g) and the resulting reaction was stirred under a balloon of hydrogen gas for 2 hours. The reaction mixture was filtered through diatomaceous earth (commercially sold under the trade mark "Celite"), washed with methanol and concentrated in vacuo. The crude product was purified by column chromatography (silica, 0-20% ethyl acetate/n-hexane) to afford the title compound.

MS ES+: 327

Step (v):
2-(Quinolin-2-ylmethyl)cyclopentan-1-amine hydrochloride

To a solution of tert-butyl N-[2-(quinolin-2-ylmethyl)cyclopentyl]carbamate (14 g, 4.28 mmol) in 1,4-dioxane (5 ml) was added HCl in 1,4-dioxane (12%, 20 ml) at 0° C. and the resulting mixture was stirred at room temperature for 1 hour. The reaction mixture was concentrated in vacuo and the crude material purified by column chromatography (silica, 0-2% methanol/DCM) to afford the cis- and trans-isomers of the title compound.

Isomer 1 Racemic $^1$H NMR (DMSO-d$_6$) δ ppm 150-1.70 (m, 2H), 175-1.86 (m, 2H), 1.94-2.02 (m, 1H), 2.61-2.68 (m, 1H), 3.17-3.25

(m, 2H), 3.46-3.60 (m, 1H), 3.63-30.70 (m, 1H), 7.82-7.89 (m, 1H), 7.90-7.96 (m, 1H), 8.04-8.06 (m, 1H), 8.20-8.45 (m, 5H), 8.85-9.01 (br, s., 1H)

MS ES+: 228

Isomer 2 Racemic $^1$H NMR (DMSO-d$_6$) δ ppm 1.39-1.50 (m, 1H), 1.60-1.72 (m, 3H), 1.72-1.83 (m, 1H), 2.02-2.15 (m, 1H), 3.14-3.25 (m, 1H), 3.32-3.44 (m, 1H), 3.60-3.90 (m, 1H), 7.81-8.01 (m, 2H), 8.02-8.12 (m, 1H), 8.23-8.49 (m, 5H), 8.85-9.05 (br. s., 1H)

MS ES+: 228

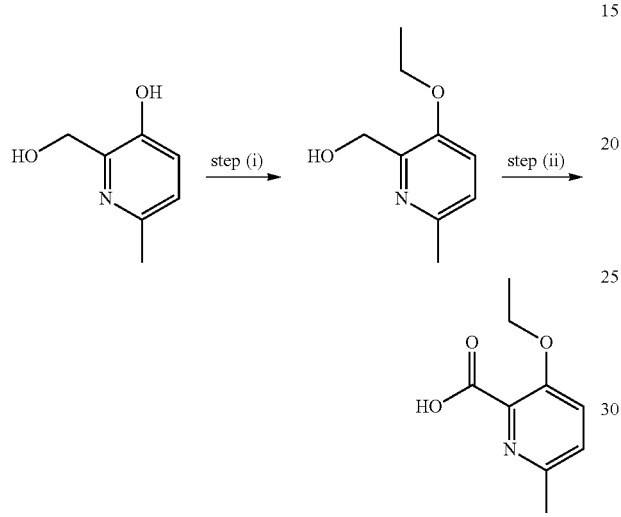

Intermediate 13:
3-Ethoxy-6-methylpyridine-2-carboxylic acid

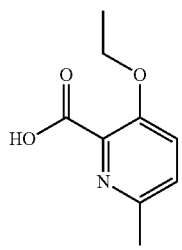

Step (i): (3-Ethoxy-6-methylpyridin-2-yl)methanol

To a solution of 2-(hydroxymethyl)-6-methylpyridin-3-ol (CAS number 42097-42-7; 1.00 g, 7.19 mmol) in DMF (10 ml) was added iodoethane (0.69 ml, 8.62 mmol) and potassium carbonate (4.97 g, 35.9 mmol). The reaction mixture was stirred at room temperature for 24 hours then partitioned between diethyl ether and water. The organics were washed with brine, dried over magnesium sulfate, filtered and concentrated in vacuo. The crude material was purified by column chromatography (silica, 0-100% ethyl acetate/petrol) to afford the title compound.

$^1$H NMR (400 MHz, DCM-d$_2$) δ ppm 1.39-1.51 (m, 3H), 2.55 (s, 3H), 4.02-4.14 (m, 2H), 4.71 (s, 2H), 7.06-7.13 (m, 1H), 7.14-7.20 (m, 1H)

Step (ii): 3-Ethoxy-6-methylpyridine-2-carboxylic acid

To a suspension of (3-ethoxy-6-methylpyridin-2-yl)methanol in water (780 μl) was added potassium hydroxide (57 mg, 1.02 mmol) and KMnO$_4$ (297 mg, 1.881 mmol) and the resultant mixture was stirred at room temperature for 2 hours. The reaction mixture was acidified to pH 4, diluted with methanol, filtered through diatomaceous earth (commercially sold under the trade mark "Celite") and concentrated in vacuo to remove any volatiles. The remaining aqueous layer was washed with DCM then concentrated in vacuo. Water was added to form a suspension. The solids were filtered off and the filtrate was adjusted to give pH 4 and extracted with DCM. The organics were concentrated in vacuo to afford the title compound.

$^1$H NMR (400 MHz, DCM-d$_2$) δ ppm 1.46-1.58 (m, 3H), 2.59 (s, 3H), 4.15-4.33 (m, 2H), 7.40-7.54 (m, 2H)

2. EXAMPLES

Example 1: 3-Bromo-N-[(1S,2S)-2-[(6-fluoro-1,3-benzothiazol-2-yl)amino]cyclopentyl]-pyridine-2-carboxamide

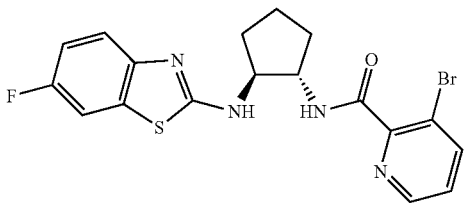 [SMILES: O=C(N[C@H]1CCC[C@@H]1Nc1nc2ccc(F)cc2s1)c1ncccc1Br]

To a solution of (1S,2S)-1-N-(6-fluoro-1,3-benzothiazol-2-yl)cyclopentane-1,2-diamine hydrochloride (Intermediate 1; 1.00 g, 3.47 mmol) in dry DCM (11.6 ml) was added 3-bromopyridine-2-carboxylic acid (CAS number 30683-23-9; 0.84 g, 4.17 mmol), HATU (1.98 g, 5.21 mmol) and DIPEA. (1.82 ml, 10.42 mmol). The reaction mixture was stirred at room temperature for 3 hours then partitioned between DCM and a saturated solution of sodium bicarbonate. The organics were filtered through a hydrophobic frit and concentrated in vacuo. The crude material was purified by column chromatography (silica, 0-100% ethyl acetate/petrol then 0-20% methanol/ethyl acetate) then by reverse phase preparative HPLC (eluted with acetonitrile/water containing 0.1% ammonia) to afford the title compound.

$^1$H NMR (DMSO-d$_6$) δ ppm 1.48-1.61 (m, 2H), 1.70-1.83 (m, 2H), 2.06-2.20 (m, 2H), 4.15-4.28 (m, 2H), 7.00-7.07 (m, 1H), 7.28-7.35 (m, 1H), 7.38-7.43 (m, 1H), 7.56-7.60 (m, 1H), 8.10-8.14 (m, 1H), 8.16-8.20 (m, 1H), 8.51-8.55 (m, 1H), 8.78-8.88 (m, 1H)

MS ES+: 436/437

Example 2: 6-Bromo-N-[(1S,2S)-2-[(6-fluoro-1,3-benzothiazol-2-yl)amino]cyclopentyl]-3-methoxy-pyridine-2-carboxamide

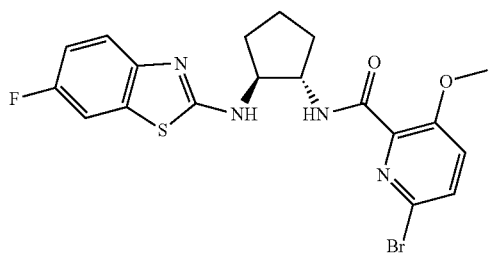 [SMILES: COc1ccc(Br)nc1C(=O)N[C@H]1CCC[C@@H]1Nc1nc2ccc(F)cc2s1]

To a solution of (1S,2S)-1-N-(6-fluoro-1,3-benzothiazol-2-yl)cyclopentane-1,2-diamine hydrochloride (Intermediate 1; 343 mg, 1.19 mmol) in dry DCM (4 ml) and THF (2 ml) was added 6-bromo-3-methoxypyridine-2-carboxylic acid (CAS number 1256810-26-0; 349 mg, 1.50 mmol), HATU (680 mg, 1.79 mmol) and triethylamine (498 µl, 3.58 mmol). The reaction mixture was stirred at room temperature for 72 hours then partitioned between DCM and a saturated solution of sodium bicarbonate. The organics were filtered through a hydrophobic frit and concentrated in vacuo. The crude material was purified by column chromatography (silica, 0-100% ethyl acetate/petrol then 0-30% methanol/ethyl acetate) and then further purified by column chromatography (silica, 0-100% ethyl acetate/petrol then 0-30% methanol/ethyl acetate) to afford the title compound.

$^1$H NMR (DMSO-d$_6$) δ ppm 1.50-1.72 (m, 2H), 1.69-1.78 (m, 2H), 2.05-2.18 (m, 2H), 3.72 (s, 3H), 4.14-4.25 (m, 2H), 6.99-7.08 (m, 1H), 7.29-7.34 (m, 1H), 7.50-7.69 (m, 3H), 8.13-8.21 (m, 1H), 8.54-8.62 (m, 1H)

MS ES$^+$: 466/468

Example 3: N-[(1S,2S)-2-[(6-Fluoro-1,3-benzothiazol-2-yl)amino]cyclopentyl]-3-methoxypyridine-2-carboxamide

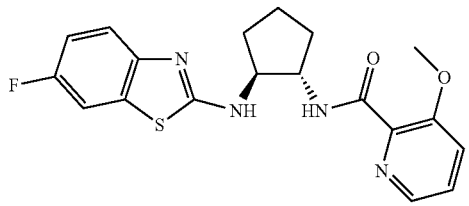 [SMILES: COc1cccnc1C(=O)N[C@H]1CCC[C@@H]1Nc1nc2ccc(F)cc2s1]

To a solution of (1S,2S)-1-N-(6-fluoro-1,3-benzothiazol-2-yl)cyclopentane-1,2-diamine hydrochloride (Intermediate 1; 250 mg, 0.87 mmol), 3-methoxypyridine-2-carboxylic acid (CAS number 16478-52-7; 160 mg, 1.04 mmol) and triethylamine (363 µl, 2.61 mmol) in DMF (3 ml) was added HATU (495 mg, 1.30 mmol). The resultant mixture was stirred at room temperature for 18 hours then partitioned between ethyl acetate and water. The organics were washed with water and a saturated solution of sodium bicarbonate, and then extracted with HCl (1 M, 20 ml). The resulting aqueous layer was concentrated in vacuo, basified with NaOH (2 M) and extracted with ethyl acetate. The organics were filtered through a hydrophobic frit and concentrated in vacuo. The crude product was purified by column chromatography (silica, 20-100% ethyl acetate/petrol) to afford the title compound.

$^1$H (DMSO-d$_6$) δ ppm 1.48-1.61 (m, 2H), 1.65-1.79 (m, 2H), 2.27-2.20 (m, 2H), 3.73 (s, 3H), 4.13-4.27 (m, 2H), 7.00-7.08 (m, 1H), 7.29-7.33 (m, 7.39-7.45 (m, 1H), 7.47-7.53 (m, 1H), 7.56-7.61 (m, 1H), 8.09-8.11 (m, 1H), 8.13-8.16 (m, 1H), 8.52-8.58 (m, 1H)

MS ES$^+$: 387

Example 4: 3-Chloro-N-[(1S,2S)-2-[(6-fluoro-1,3-benzothiazol-2-yl)amino]cyclopentyl]-pyridine-2-carboxamide

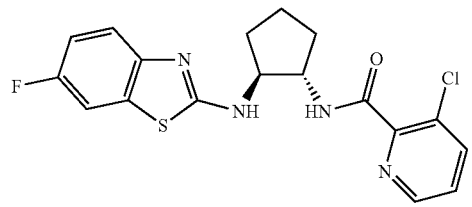

To a solution of (1S,2S)-1-N-(6-fluoro-1,3-benzothiazol-2-yl)cyclopentane-1,2-diamine hydrochloride (Intermediate 1; 50 mg, 0.17 mmol), 3-chloropyridine-2-carboxylic acid (CAS number 57266-69-0; 41 mg, 0.26 mmol) and triethylamine (0.073 ml, 0.52 mmol) in DCM (2 ml) was added HATU (99 mg, 0.26 mmol). The reaction mixture was stirred at room temperature for 3 hours then partitioned between DCM and a saturated solution of sodium bicarbonate. The organics were filtered through a hydrophobic frit and concentrated in vacuo. The crude material was purified by reverse phase preparative HPLC (eluted with acetonitrile/water containing 0.1% ammonia) to afford the title compound.

$^1$H NMR (MeOH-d$_4$) δ ppm 1.65-1.80 (m, 2H), 1.85-1.95 (m, 2H), 2.14-2.26 (m, 2H), 4.14-4.24 (m, 2H), 6.93-7.01 (m, 1H), 7.25-7.40 (m, 2H), 7.43-7.48 (m, 1H), 7.88-7.94 (m, 1H), 8.46-8.49 (m, 1H).

MS ES$^+$: 391

Example 5: N-[(1S,2S)-2-[(6-Fluoro-1,3-benzothiazol-2-yl)amino]cyclopentyl]-3-methoxy-N-methyl-pyridine-2-carboxamide

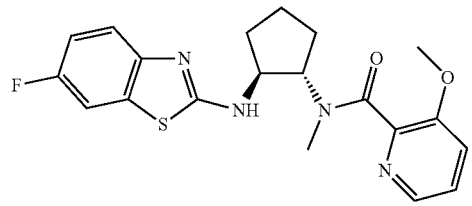 [SMILES: COc1cccnc1C(=O)N(C)[C@H]1CCC[C@@H]1Nc1nc2ccc(F)cc2s1]

To a solution of (1S,2S)-1-N-(6-fluoro-1,3-benzothiazol-2-yl)-2-N-methyl-cyclopentane-1,2-diamine (Intermediate 3; 50 mg, 0.17 mmol), 3-methoxypyridine-2-carboxylic acid (CAS number 16478-52-7; 30 mg, 0.20 mmol) and triethylamine (0.069 ml, 0.50 mmol) in DMF (1 ml) was added HAM (94 mg, 0.25 mmol). The reaction mixture was stirred at room temperature for 18 hours then partitioned between DCM and water. The organics were washed with a saturated solution of sodium bicarbonate, filtered through a hydrophobic frit and concentrated in vacuo. The crude material was purified by reverse phase preparative HPLC (eluted with acetonitrile/water containing 0.1% ammonia) to afford the title compound.

$^1$H NMR (400 MHz, DMSO-$d_6$) δ ppm 1.45-2.18 (m, 6H), 2.63-2.99 (m, 3H), 3.47-3.66 (m, 3H), 3.70-4.89 (m, 2H), 6.97-8.17 (m, 7H)

MS ES$^+$: 401

Example 6: N-[(1S,2S)-2-[(6-Fluoro-1,3-benzothiazol-2-yl)amino]cyclopentyl]-3-(2H-1,2,3-triazol-2-yl)pyridine-2-carboxamide

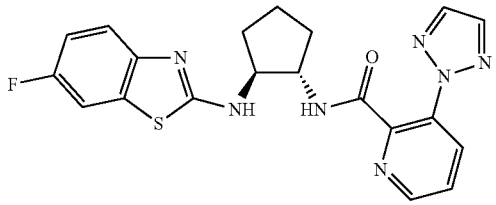 [SMILES: O=C(N[C@H]1CCC[C@@H]1Nc1nc2ccc(F)cc2s1)c1ncccc1-n1nccn1]

A microwave vial was charged with 3-bromo-N-[(1S,2S)-2-[(6-fluoro-1,3-benzothiazol-2-yl)amino]cyclopentyl]pyridine-2-carboxamide (Example 1; 900 mg, 2.07 mmol), 2H-1,2,3-triazole (CAS number 288-36-8; 286 mg, 4.13 mmol), cesium carbonate (1347 mg, 4.13 mmol), copper(I) iodide (20 mg, 0.10 mmol) and trans-1-N,2-N-dimethylcyclohexane-1,2-diamine (59 mg, 0.41 mmol) in DMF (7 The reaction mixture was subjected to microwave irradiation at 120° C. for 1 hour then partitioned between ethyl acetate and water. The organics were washed with water and brine, dried over magnesium sulfate, filtered and concentrated in vacuo. The crude product was purified by column chromatography (silica, 50-100% ethyl acetate/petrol then 0-30% methanol/ethyl acetate), the resultant solid was recrystallised from ethyl acetate to afford the title compound.

$^1$H NMR (DMSO-$d_6$) δ ppm 1.45-1.55 (m, 2H), 1.64-1.73 (m, 2H), 1.96-2.15 (m, 2H), 3.99-4.08 (m, 1H), 4.16-4.26 (m, 1H), 7.01-7.08 (m, 1H), 7.32-7.36 (m, 1H), 7.56-7.61 (m, 1H), 7.75-7.78 (m, 1H), 7.81 (s, 1H), 8.10-8.19 (m, 2H), 8.45 (s, 1H), 8.86-8.88 (m, 1H), 9.05-9.09 (m, 1H)

MS ES$^+$: 424

Example 7: N-[(1S,2S)-2-[(6-Fluoro-1,3-benzoxazol-2-yl)amino]cyclopentyl]-3-methoxypyridine-2-carboxamide

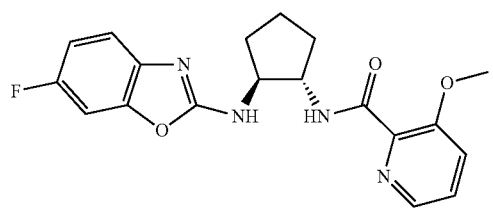 [SMILES: COc1cccnc1C(=O)N[C@H]1CCC[C@@H]1Nc1nc2ccc(F)cc2o1]

To a solution of N-[(1S,2S)-2-aminocyclopentyl]-3-methoxypyridine-2-carboxamide hydrochloride (Intermediate 2; 75 mg, 0.28 mmol) and DIPEA (0.15 ml, 0.83 mmol) in DMSO (1 ml) was added 2-chloro-6-fluoro-1,3-benzoxazole (CAS number 153403-53-3; 57 mg, 0.33 mmol) and the reaction mixture was subjected to microwave irradiation at 140° C., for 2 hours. The reaction mixture was partitioned between DCM and water. The 1.5 organics were filtered through a hydrophobic frit and concentrated in vacuo. The crude material was purified by reverse phase preparative HPLC (eluted with acetonitrile/water containing 0.1% ammonia) to afford the title compound.

$^1$H NMR (DCM-$d_2$) δ ppm 1.66-1.82 (m, 2H), 1.86-1.94 (m, 2H), 2.21-2.32 (m, 1H), 2.46-2.58 (m, 1H), 3.91 (s, 3H), 3.91-3.99 (m, 1H), 4.35-4.45 (m, 1H), 6.55-6.66 (m, 1H), 6.85-6.93 (m, 1H), 6.98-7.02 (m, 1H), 7.16-7.20 (m, 1H), 7.45-7.56 (m, 2H), 8.08-8.19 (m, 1H), 8.15-8.23 (m, 1H)

MS ES$^+$: 371

Example 8: N-[(1S,2S)-2-[(6-Fluoro-1,3-benzothiazol-2-yl)amino]cyclopentyl]-3-(propan-2-yloxy)pyridine-2-carboxamide

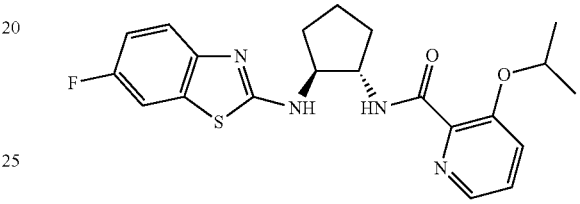

To a slurry of (1S,2S)-1-N-(6-fluoro-1,3-benzothiazol-2-yl)cyclopentane-1,2-diamine hydrochloride (Intermediate 1; 100 mg, 0.35 mmol) in dry DCM (1.2 ml) was added 3-isopropoxypyridine-2-carboxylic acid (CAS number 317334-97-7; 70 mg, 0.39 mmol), HATU (198 mg, 0.52 mmol) and triethylamine (145 µl, 1.04 mmol). The reaction mixture was stirred at room temperature for 72 hours then partitioned between DCM and a saturated solution of sodium carbonate. The organics were filtered through a hydrophobic frit and concentrated in vacuo. The crude product was purified by column chromatography (silica, 0-100% ethyl acetate/petrol then 0-30% methanol/ethyl acetate) then by reverse phase preparative HPLC (eluted with acetonitrile/water containing 0.1% ammonia) to afford the title compound.

$^1$H NMR (DMSO-$d_6$) δ ppm 1.15-1.21 (m, 6H), 1.51-1.65 (m, 2H), 1.68-1.78 (m, 2H), 2.15-2.21 (m, 2H) 4.14-4.23 (m, 2H) 4.53-4.68 (m, 1H), 6.95-7.08 (m, 1H) 7.28-7.33 (m, 1H), 7.35-7.42 (m, 1H), 7.50-7.56 (m, 1H), 7.58-7.61 (m, 1H), 8.08-8.12 (m, 1H), 8.16-8.19 (m, 1H), 8.43-8.48 (m, 1H)

MS ES$^+$: 415

Example 9: N-[(1S,2S)-2-[(6-Fluoro-1,3-benzothiazol-2-yl)amino]cyclopentyl]-3-methoxy-6-methyl-pyridine-2-carboxamide

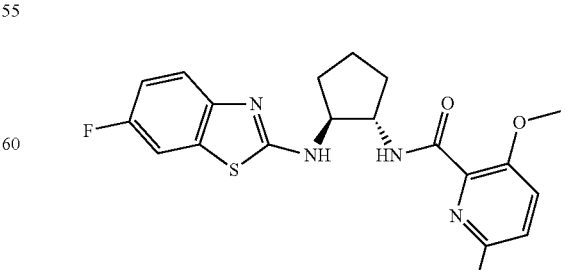

A microwave vial was charged with 6-bromo-N-[(1S,2S)-2-[(6-fluoro-1,3-benzothiazol-2-yl)amino]cyclopentyl]-3-methoxypyridine-2-carboxamide (Example 2; 80 mg, 0.17 mmol), methyl boronic acid (21 mg, 0.35 mmol), potassium carbonate (95 mg, 0.69 mmol), tetrakis(triphenylphosphine)palladium(0) (20 mg, 0.017 mmol), 1,4-dioxane (500 µl) and water (115 µl). The reaction was sealed, evacuated and purged with nitrogen and subjected to microwave irradiation at 100° C. for 1 hour. The reaction mixture was partitioned between ethyl acetate and water then the organics washed with water, filtered through a hydrophobic frit and concentrated in vacuo. The crude material was purified by column chromatography (silica, 0-100% ethyl acetate/petrol then 0-20% methanol/ethyl acetate) to afford the title compound.

$^1$H NMR (DMSO-d$_6$) δ ppm 1.56-1.71 (m, 2H), 1.69-1.78 (m, 2H), 2.06-2.18 (m, 2H), 2.38 (s, 3H), 3.69 (s, 3H), 4.12-4.28 (m, 2H), 6.99-7.08 (m, 1H), 7.23-7.35 (m, 2H), 7.38-7.41 (m, 1H) 7.56-7.60 (m, 1H) 8.15-8.19 (m, 1H), 8.43-8.46 (m, 1H)

MS ES$^+$: 401

Example 10: N-[(1S,2S)-2-[(6-Fluoro-1,3-benzothiazol-2-yl)amino]cyclopentyl]-3-(1H-pyrazol-1-yl)pyridine-2-carboxamide

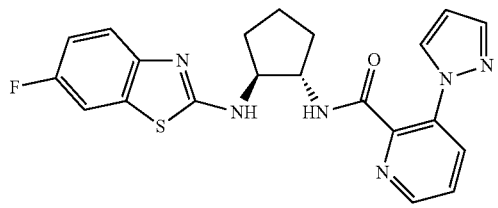 [SMILES: O=C(N[C@H]1CCC[C@@H]1Nc1nc2ccc(F)cc2s1)c1ncccc1-n1cccn1]

A microwave vial was charged with 3-bromo-N-[(1S,2S)-2-[(6-fluoro-1,3-benzothiazol-2-yl)amino]cyclopentyl]pyridine-2-carboxamide (Example 1; 100 mg, 0.23 mmol), 1H-pyrazole (CAS number 288-13-1; 31 mg, 0.46 mmol), cesium carbonate (150 mg, 0.46 mmol), copper (I) iodide (2 mg, 0.010 mmol) and trans-1-N,2-N-dimethylcyclohexane-1,2-diamine (2 mg, 0.013 mmol) in DMF (780 µl). The reaction mixture was subjected to microwave irradiation at 120° C. for 1 hour then partitioned between ethyl acetate and water. The organics were washed with brine, filtered through a hydrophobic frit and concentrated in vacuo. The crude material was purified by reverse phase preparative HPLC (eluted with acetonitrile/water containing 0.1% ammonia) to afford the title compound.

$^1$H NMR (400 MHz, DCM-d$_2$) δ ppm 1.46-1.80 (m, 2H), 1.82-2.01 (m, 2H), 2.19-2.50 (m, 2H), 4.05-4.21 (m, 1H), 4.23-4.40 (m, 1H), 6.23-6.40 (m, 1H), 6.40-6.51 (m, 1H), 7.52-7.63 (m, 1H), 7.65-7.71 (m, 1H), 7.74-7.82 (m, 1H), 7.87-7.93 (m, 1H), 7.94-8.01 (m, 1H), 8.03-8.13 (m, 1H), 8.25-8.33 (m, 1H), 8.54-8.64 (m, 1H)

MS ES$^+$: 423

Example 11: 3-Fluoro-N-[(1S,2S)-2-[(6-fluoro-1,3-benzothiazol-2-yl)amino]cyclopentyl]pyridine-2-carboxamide

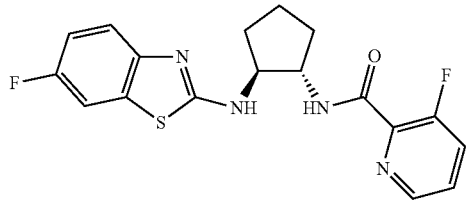

To a solution of (1S,2S)-1-N-(6-Fluoro-1,3-benzothiazol-2-yl)cyclopentane-1,2-diamine hydrochloride (Intermediate 1; 50 mg, 0.17 mmol), 3-fluoropyridine-2-carboxylic acid (CAS number 152126-31-3; 37 mg, 0.26 mmol) and triethylamine (0.073 ml, 0.52 mmol) in DCM (2 ml) was added HATU (99 mg, 0.26 mmol). The reaction mixture was stirred at room temperature for 24 hours then partitioned between DCM and water. The organics were filtered through a hydrophobic frit and concentrated in vacuo. The crude material was purified by reverse phase preparative HPLC (eluted with acetonitrile/water containing 0.1% ammonia) to afford the title compound.

$^1$H NMR (400 MHz, DMSO-d$_6$) δ ppm 1.46-1.67 (m, 2H), 1.68-1.82 (m, 2H), 2.05-2.25 (m, 2H), 4.09-4.23 (m, 1H), 4.25-4.38 (m, 1H), 6.98-7.10 (m, 1H), 7.29-7.37 (m, 1H), 7.54-7.60 (m, 1H), 7.61-7.69 (m, 1H), 7.75-7.89 (m, 1H), 8.14-8.26 (m, 1H), 8.38-8.49 (m, 1H), 8.94-9.06 (m, 1H)

MS ES$^+$: 375

Example 12: N-[(1S,2S)-2-[(6-Fluoro-1,3-benzothiazol-2-yl)amino]cyclopentyl]-3-(piperidin-1-yl)pyridine-2-carboxamide

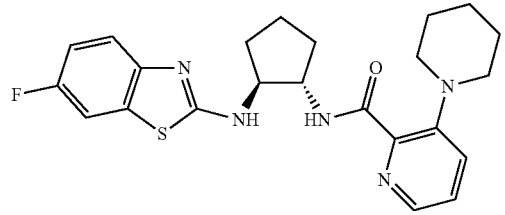 [SMILES: O=C(N[C@H]1CCC[C@@H]1Nc1nc2ccc(F)cc2s1)c1ncccc1N1CCCCC1]

A mixture of 3-(piperidin-1-yl)pyridine-2-carboxylic acid (CAS number 898289-01-5; 59 mg, 0.29 mmol), (1S,2S)-1-N-(6-fluoro-1,3-benzothiazol-2-yl)cyclopentane-1,2-diamine hydrochloride (Intermediate 1; 75 mg, 0.26 mmol), EDC (75 mg, 0.392 mmol), 3H-[1,2,3]triazolo[4,5-b]pyridin-3-ol (53 mg, 0.390 mmol) and triethylamine (0.11 ml, 0.78 mmol) in dry DCM (1 ml) was stirred at room temperature for 18 hours then partitioned between DCM and a saturated solution of sodium bicarbonate. The organics were filtered through a hydrophobic frit and concentrated in vacuo. The crude material was purified by column chromatography (silica, 40-100% ethyl acetate/petrol) and then purified further by reverse phase preparative HPLC (eluted with acetonitrile/water containing 0.1% ammonia) to afford the title compound.

¹H NMR (400 MHz, DCM-d₂) δ ppm 1.54-1.67 (m, 2H), 1.69-1.85 (m, 6H), 1.87-2.04 (m, 2H), 2.21-2.40 (m, 1H), 2.49-2.65 (m, 1H), 2.92-3.11 (m, 4H), 3.93-4.11 (m, 1H), 4.34-4.52 (m, 1H), 6.90-7.09 (m, 1H), 7.24-7.45 (m, 3H), 7.46-7.56 (m, 1H), 8.17-8.34 (m, 1H)

MS ES⁺: 440

Example 13: 3-(Azetidin-1-yl)-N-[(1S,2S)-2-[(6-fluoro-1,3-benzothiazol-2-yl)amino]cyclopentyl]pyridine-2-carboxamide

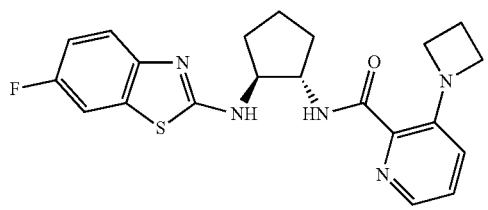 [SMILES: O=C(N[C@H]1CCC[C@@H]1Nc1nc2ccc(F)cc2s1)c1ncccc1N1CCC1]

A microwave vial was charged with 3-bromo-N-[(1S,2S)-2-[(6-fluoro-1,3-benzothiazol-yl)amino]cyclopentyl]-pyridine-2-carboxamide (Example 1; 200 mg, 0.46 mmol), azetidine (CAS number 503-29-7; 393 mg, 6.89 mmol), RuPhos-Palladacycle (4 mg, 5.48 μmol), sodium tert-butoxide (88 mg, 0.92 mmol) and dicyclohexyl(2',6'-diisopropoxy-[1,1'-biphenyl]-2-yl)phosphine (7 mg, 0.015 mmol) in THF (1.5 ml). The reaction mixture was subjected to microwave irradiation at 100° C. for 1 hour then partitioned between ethyl acetate and water. The organics were washed with water then brine, filtered through a hydrophobic frit and concentrated in vacuo. The crude material was purified by reverse phase preparative HPLC (eluted with acetonitrile/water containing 0.1% ammonia) to afford the title compound.

¹H NMR (400 MHz, DCM-d₂) δ ppm 1.68-1.83 (m, 2H), 1.89-2.00 (m, 2H), 2.21-2.38 (m, 3H), 2.44-2.56 (m, 1H), 3.89-4.10 (m, 5H), 4.27-4.40 (m, 1H), 6.87-6.94 (m, 1H), 6.98-7.08 (m, 1H), 7.22-7.29 (m, 2H), 7.29-7.35 (m, 1H), 7.38-7.46 (m, 1H), 7.86-7.92 (m, 1H), 7.93-8.04 (m, 1H)

MS ES⁺: 412

Example 14: N-[(1S,2S)-2-[(6-Fluoro-1,3-benzothiazol-2-yl)amino]cyclopentyl]-3-(pyrrolidin-1-yl)pyridine-2-carboxamide

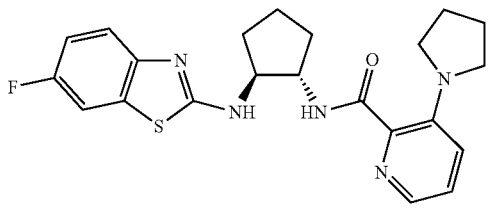 [SMILES: O=C(N[C@H]1CCC[C@@H]1Nc1nc2ccc(F)cc2s1)c1ncccc1N1CCCC1]

A microwave vial was charged with 3-bromo-N-[(1S,2S)-2-[(6-fluoro-1,3-benzothiazol-2-yl)amino]cyclopentyl]-pyridine-2-carboxamide (Example 1; 200 mg, 0.46 mmol), RuPhos-Palladacycle (4 mg, 5.48 μmol), sodium tert-butoxide (88 mg, 0.92 mmol), dicyclohexyl(2',6'-diisopropoxy-[1,1'-biphenyl]-2-yl)phosphine (7 mg, 0.015 mmol) and pyrrolidine (CAS number 123-75-1; 490 mg, 6.89 mmol) in THF (1.5 ml). The reaction mixture was subjected to microwave irradiation at 100° C. for 1 hour then partitioned between ethyl acetate and water. The organics were washed with water then brine, filtered through a hydrophobic frit and concentrated in vacuo. The crude material was purified by reverse phase preparative HPLC (eluted with acetonitrile/water containing 0.1% ammonia) to afford the title compound.

¹H NMR (400 MHz, DCM-d₂) δ ppm 1.71-2.04 (m, 8H), 2.25-2.39 (m, 1H), 2.41-2.55 (m, 1H), 3.15-3.27 (m, 2H), 3.28-3.42 (m, 2H), 3.98-4.11 (m, 1H), 4.29-4.42 (m, 1H), 7.02-7.11 (m, 1H), 7.17-7.21 (m, 1H), 7.22-7.28 (m, 1H), 7.31-7.37 (m, 1H), 7.40-7.46 (m 1H), 7.70-7.77 (m, 1H), 7.86-7.92 (m, 1H)

MS ES⁺: 426

Example 15: N-[(1S,2S)-2-[(6-Fluoro-1,3-benzothiazol-2-yl)amino]cyclopentyl]-3-(3-methoxyazetidin-1-yl)pyridine-2-carboxamide

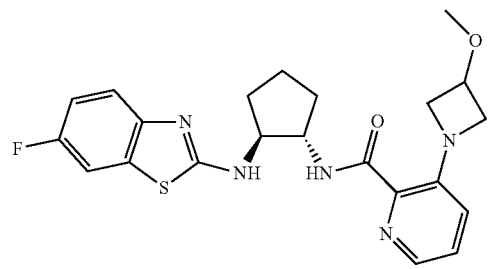 [SMILES: COC1CN(c2cccnc2C(=O)N[C@H]2CCC[C@@H]2Nc2nc3ccc(F)cc3s2)C1]

A microwave vial was charged with 3-bromo-N-[(1S,2S)-2-[(6-fluoro-1,3-benzothiazol-2-yl)amino]cyclopentyl]-pyridine-2-carboxamide (Example 1; 200 mg, 0.46 mmol), 3-methoxyazetidine (CAS number 110925-17-2; 600 mg, 6.89 mmol), RuPhos-Palladacycle (4 mg, 5.48 μmol), sodium tert-butoxide (530 mg, 5.51 mmol), dicyclohexyl(2',6'-diisopropoxy-[1,1'-biphenyl]-2-yl)phosphine (7 mg, 0.015 mmol) and THF (1.5 ml). The reaction mixture was subjected to microwave irradiation at 100° C. for 1 hour then partitioned between ethyl acetate and water. The organics were washed with water then brine, filtered through a hydrophobic frit and concentrated in vacuo. The crude material was purified by reverse phase preparative HPLC (eluted with acetonitrile/water containing 0.1% ammonia) to afford the title compound.

¹H NMR (400 MHz, DCM-d₂) δ ppm 1.68-1.83 (m, 2H), 1.89-2.00 (m, 2H), 2.22-2.37 (m, 1H), 2.45-2.59 (m, 1H), 3.70-3.77 (m, 1H), 3.79-3.88 (m, 1H), 3.94-4.05 (m, 1H), 4.12-4.41 (m, 5H), 6.85-6.95 (m, 1H), 6.98-7.07 (m, 1H), 7.21-7.36 (m, 2H), 7.38-7.47 (m, 1H), 7.88-7.95 (m, 1H), 7.98-8.06 (m, 1H)

MS ES⁺: 442

Example 16: 3-Methoxy-N-[(1S,2S)-2-[(quinoxalin-2-yl)amino]cyclopentyl]pyridine-2-carboxamide

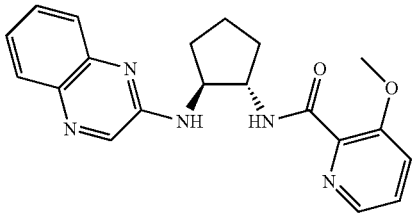 [SMILES: COc1cccnc1C(=O)N[C@H]1CCC[C@@H]1Nc1cnc2ccccc2n1]

A microwave vial was charged with N-[(1S,2S)-2-aminocyclopentyl]-3-methoxypyridine-2-carboxamide hydrochloride (Intermediate 2; 75 mg, 0.28 mmol) and DIPEA (0.15 ml, 0.83 mmol) in DMSO (1.0 ml). 2-chloroquinoxaline (CAS number 1448-87-9; 54 mg, 0.33 mmol) was added and the reaction mixture subjected to microwave irradiation at 140° C. for 2 hours. The reaction mixture was partitioned between DCM and water then the organics filtered through a hydrophobic frit and concentrated in vacuo. The crude material was purified by reverse phase preparative HPLC (eluted with acetonitrile/water containing 0.1% ammonia) then purified further by column chromatography (silica, 0-15% methanol/DCM) to afford the title compound.

$^1$H NMR (400 MHz, DCM-d$_2$) δ ppm 1.66-1.83 (m, 2H), 1.88-2.03 (m, 2H), 2.31-2.44 (m, 1H), 2.48-2.61 (m, 1H), 3.85 (s, 3H), 4.27-4.44 (m, 2H), 6.02-6.17 (m, 1H), 7.29-7.43 (m, 3H), 7.49-7.59 (m, 1H), 7.60-7.69 (m, 1H), 7.78-7.88 (m, 1H), 8.06-8.16 (m, 1H), 8.20-8.29 (m, 1H), 8.34-8.45 (m, 1H)

MS ES$^+$: 364

Example 17: N-[(1S,2S)-2-[(6-Fluoro-1,3-benzothiazol-2-yl)amino]cyclopentyl]-3-methoxy-6-(trifluoromethyl)pyridine-2-carboxamide

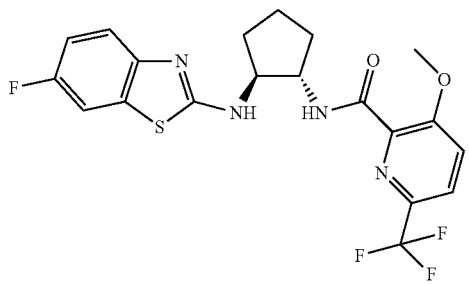 [SMILES: COc1ccc(C(F)(F)F)nc1C(=O)N[C@H]1CCC[C@@H]1Nc1nc2ccc(F)cc2s1]

A microwave vial was charged with (1S,2S)-1-N-(6-fluoro-1,3-benzothiazol-2-yl)cyclopentane-1,2-diamine hydrochloride (Intermediate 1; 952 mg, 3.31 mmol), molybdenum hexacarbonyl (437 mg, 1.65 mmol), tri-tert-butylphosphonium tetrafluoroborate (29 mg, 0.10 mmol), 2-chloro-3-methoxy-6-(trifluoromethyl)pyridine (Intermediate 4; 700 mg, 3.31 mmol), Herrmanns Catalyst (31 mg, 0.033 mmol) and DBU (0.83 ml, 5.53 mmol) in dry 1,4-dioxane (13 ml). The reaction mixture was subjected to microwave irradiation at 125° C. for 1 hour then partitioned between ethyl acetate and water. The organics were washed with water and brine, filtered through a hydrophobic frit and concentrated in vacuo. The crude material was purified by reverse phase preparative HPLC (eluted with acetonitrile/water containing 0.1% ammonia) then further purified by column chromatography (silica, 0-100% ethyl acetate/petrol then 0-30% methanol/ethyl acetate) to afford the tide compound.

$^1$H NMR (400 MHz, DMSO-d$_6$) δ ppm 1.49-1.64 (m, 2H), 1.68-1.81 (m, 2H), 2.04-2.22 (m, 2H), 3.78 (s, 3H), 4.12-4.27 (m, 2H), 6.97-7.09 (m, 1H), 7.24-7.35 (m, 1H), 7.53-7.62 (m, 1H), 7.66-7.75 (m, 1H), 7.88-7.99 (m, 1H), 8.13-8.25 (m, 1H), 8.56-8.71 (m, 1H)

MS ES$^+$: 455

Example 18: 3-Ethoxy-N-[(1S,2S)-2-[(6-fluoro-1,3-benzothiazol-2-yl)amino]cyclopentyl]pyridine-2-carboxamide

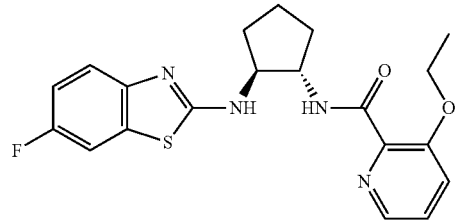 [SMILES: CCOc1cccnc1C(=O)N[C@H]1CCC[C@@H]1Nc1nc2ccc(F)cc2s1]

To a slurry of (1S,2S)-1-N-(6-fluoro-1,3-benzothiazol-2-yl)cyclopentane-1,2-diamine hydrochloride (Intermediate 1; 100 mg, 0.35 mmol) in dry DCM (1.2 ml) was added 3-ethoxypyridine-2-carboxylic acid hydrochloride (Intermediate 5, 78 mg, 0.38 mmol), HATU (198 mg, 0.52 mmol) and triethylamine (145 μl, 1.04 mmol). The reaction mixture was stirred at room temperature for 17 hours then partitioned between DCM and a saturated solution of sodium bicarbonate. The organics were filtered through a hydrophobic frit and concentrated in vacuo. The crude material was purified by reverse phase preparative HPLC (eluted with acetonitrile/water containing 0.1% ammonia) to afford the title compound.

$^1$H NMR (400 MHz, DCM-d$_2$) δ ppm 1.43-1.55 (m, 3H), 1.64-1.77 (m, 2H), 1.86-1.98 (m, 2H), 2.23-2.36 (m, 1H), 2.45-2.60 (m, 1H), 3.96-4.00 (m, 1H), 4.10-4.23 (m, 2H), 4.31-4.48 (m, 1H), 6.94-7.07 (m, 1H), 7.24-7.33 (m, 1H), 7.35-7.46 (m, 3H), 8.06-8.24 (m, 2H)

MS ES$^+$: 401

Example 19: N-[(1S,2S)-2-[(6-Fluoro-1,3-benzothiazol-2-yl)amino]cyclopentyl]-3-(trifluoromethoxy)pyridine-2-carboxamide

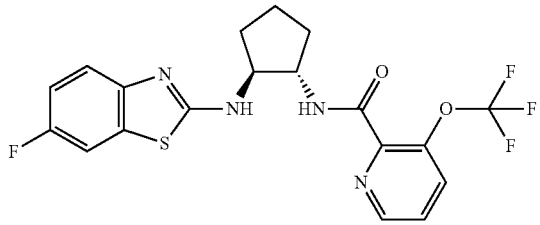 [SMILES: O=C(N[C@H]1CCC[C@@H]1Nc1nc2ccc(F)cc2s1)c1ncccc1OC(F)(F)F]

A microwave vial was charged with (1S,2S)-1-N-(6-fluoro-1,3-benzothiazol-2-yl)cyclopentane-1,2-diamine hydrochloride (Intermediate 1; 172 mg, 0.60 mmol), molybdenum hexacarbonyl (79 mg, 0.30 mmol), tri-tert-butylphosphonium tetrafluoroborate (5 mg, 0.018 mmol), 2-bromo-3-(trifluoromethoxy)pyridine (145 mg, 0.60 mmol), Herrmanns Catalyst (6 mg, 6.41 μmol) and DBU (150 μl, 0.998 mmol) in dry 1,4-dioxane (2.4 ml). The reaction was subjected to microwave irradiation at 125° C. for 25 minutes then partitioned between ethyl acetate and water. The organics were washed with water and brine, filtered through a hydrophobic frit and concentrated in vacuo. The crude material was purified by column chromatography (silica, 0-100% ethyl acetate/petrol then 0-30% methanol/ethyl acetate) then further purified by reverse phase preparative HPLC (eluted with acetonitrile/water containing 0.1% ammonia) to afford the title compound.

¹H NMR (400 MHz, DMSO-d₆) δ ppm 1.50-1.64 (m, 2H), 1.68-1.80 (m, 2H), 2.07-2.21 (m, 2H), 4.13-4.23 (m, 1H), 4.23-4.33 (m, 1H), 6.97-7.10 (m, 1H), 7.26-7.37 (m, 1H), 7.52-7.62 (m, 1H), 7.64-7.74 (m, 1H), 7.90-8.03 (m, 1H), 8.14-8.23 (m, 1H), 8.55-8.69 (m, 1H), 8.92-9.02 (m, 1H)

MS ES⁺: 441

Example 20: 3-(Difluoromethoxy)-N-[(1S,2S)-2-[(6-fluoro-1,3-benzothiazol-2-yl)amino]cyclopentyl]pyridine-2-carboxamide

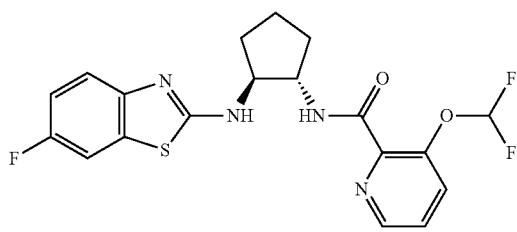 [SMILES: O=C(N[C@H]1CCC[C@@H]1Nc1nc2ccc(F)cc2s1)c1ncccc1OC(F)F]

To a solution of (1S,2S)-1-N-(6-fluoro-1,3-benzothiazol-2-yl)cyclopentane-1,2-diamine hydrochloride (Intermediate 1; 284 mg, 0.99 mmol) in dry DCM (3.3 ml) was added 3-(difluoromethoxy)pyridine-2-carboxylic acid, sodium (Intermediate 7; 209 mg, 0.99 mmol), 3H-[1,2,3]triazolo[4,5-b]pyridin-3-ol (201 mg, 1.48 mmol), EDC (283 mg, 1.48 mmol) and DIPEA (516 µl, 2.96 mmol). The reaction mixture was stirred at room temperature for 72 hours then partitioned between DCM and a saturated solution of sodium bicarbonate. The organics were filtered through a hydrophobic frit and concentrated in vacuo. The crude material was purified by column chromatography (silica, 0-100% ethyl acetate/petrol, then 0-30% methanol/ethyl acetate) to afford the title compound.

¹H NMR (400 MHz, DMSO-d₆) δ ppm 1.51-1.65 (m, 2H), 1.68-1.80 (m, 2H), 2.08-2.22 (m, 2H), 4.13-4.22 (m, 1H), 4.22-4.31 (m, 1H), 6.89-7.17 (m, 2H), 7.29-7.37 (m, 1H), 7.53-7.66 (m, 2H), 7.69-7.79 (m, 1H), 8.15-8.24 (m, 1H), 8.43-8.52 (m, 1H), 8.80-8.96 (m, 1H)

MS ES⁺: 423

Example 21: N-[(1S,2S)-2-[(6-Chloro-1,3-benzothiazol-2-yl)amino]cyclopentyl]-3-(2H-1,2,3-triazol-2-yl)pyridine-2-carboxamide

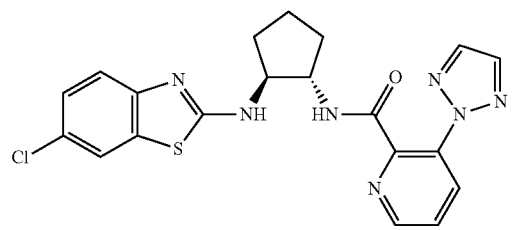 [SMILES: O=C(N[C@H]1CCC[C@@H]1Nc1nc2ccc(Cl)cc2s1)c1ncccc1-n1nccn1]

To a solution of (1S,2S)-1-N-(6-chloro-1,3-benzothiazol-2-yl)cyclopentane-1,2-diamine hydrochloride (Intermediate 9; 100 mg, 0.329 mmol) in dry DCM (1.1 ml) was added 3-(2H-1,2,3-triazol-2-yl)pyridine-2-carboxylic acid (Intermediate 10; 70 mg, 0.37 mmol), EDC (95 mg, 0.49 mmol), 3H-[1,2,3]triazolo[4,5-b]pyridin-3-ol (67 mg, 0.49 mmol) and DIPEA (172 µl, 0.99 mmol). The reaction mixture was stirred at room temperature for 4 hours then partitioned between DCM and water. The organics were filtered through a hydrophobic frit and concentrated in vacuo. The crude material was purified by column chromatography (basic silica, 0-100% ethyl acetate/petrol) to afford the title compound.

¹H NMR (400 MHz, DMSO-d₆) δ ppm 1.49-1.65 (m, 2H), 1.66-1.76 (m, 2H), 2.01-2.19 (m, 2H), 4.09-4.17 (m, 1H), 4.18-4.25 (m, 1H), 7.17-7.27 (m, 1H), 7.30-7.38 (m, 1H), 7.64-7.75 (m, 1H), 7.76-7.83 (m, 1H), 8.04 (s, 2H), 8.17-8.35 (m, 2H), 8.59-8.71 (m, 1H), 8.73-8.88 (m, 1H)

MS ES⁺: 440

Example 22: N-[(1S,2S)-2-[(6-Chloro-1,3-benzothiazol-2-yl)amino]cyclopentyl]-3-(difluoromethoxy)pyridine-2-carboxamide

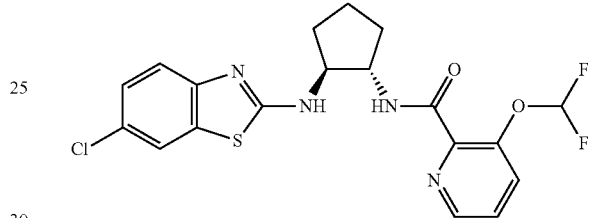

To a solution of N-[(1S,2S)-2-aminocyclopentyl]-2-(difluoromethoxy)benzamide hydrochloride (Intermediate 11; 45 mg, 0.15 mmol) in DMSO (0.5 ml) was added DIPEA (0.077 ml, 0.44 mmol) and 2,6-dichloro-1,3-benzothiazole (CAS number 3622-23-9; 36 mg, 0.18 mmol). The reaction mixture was heated to 140° C. for 4 hours then partitioned between ethyl acetate and water. The organics were washed with water and brine, dried over sodium sulfate, filtered and concentrated in vacuo. The crude material was purified by column chromatography (silica, 30-70% ethyl acetate/petrol) then purified further by reverse phase chromatography (C18 silica, 0-100% water (with 0.05% ammonia)/acetonitrile) to afford the title compound.

¹H NMR (400 MHz, DMSO-d₆) δ ppm 1.51-1.66 (m, 2H), 1.68-1.79 (m, 2H), 2.06-2.23 (m, 2H), 4.14-4.22 (m, 1H), 4.23-4.32 (m, 1H), 6.89-7.37 (m, 3H), 7.57-7.66 (m, 1H), 7.70-7.80 (m, 2H), 8.27-8.38 (m, 1H), 8.44-8.55 (m, 1H), 8.85-8.98 (m, 1H)

MS ES⁺: 439

Example 23: 3-(Difluoromethoxy)-N-[(1S,2S)-2-[(6-fluoro-1,3-benzoxazol-2-yl)amino]cyclopentyl]pyridine-2-carboxamide

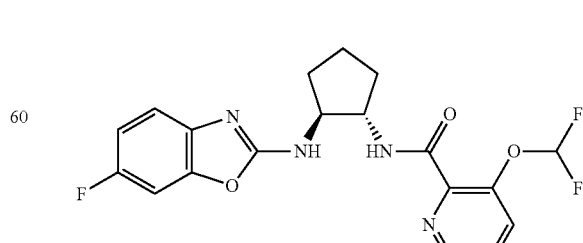

To a solution of N-[(1S,2S)-2-aminocyclopentyl]-2-(difluoromethoxy)benzamide hydrochloride (Intermediate 11; 45 mg, 0.15 mmol) in DMSO (0.5 ml) was added DIPEA (57 mg, 0.44 mmol) and 2-chloro-6-fluoro-1,3-benzoxazole (CAS number 153403-53-3; 30 mg, 0.17 mmol). The reaction mixture was heated to 140° C. for 4 hours then partitioned between ethyl acetate and water. The organics were washed with water and brine, dried over sodium sulfate, filtered and concentrated in vacuo. The crude material was purified by column chromatography (silica, 30-80% ethyl acetate/petrol) then purified further by reverse phase chromatography (C18 silica, 5-95% water (with 005% ammonia)/acetonitrile) to afford the title compound.

$^1$H NMR (400 MHz, DMSO-d$_6$) δ ppm 1.53-1.67 (m, 2H), 1.67-1.81 (m, 2H), 2.01-2.18 (m, 2H), 4.06-4.19 (m, 1H), 4.22-4.32 (m, 1H), 6.88-7.38 (m, 4H), 7.52-7.65 (m, 1H), 7.67-7.79 (m, 1H), 8.03-8.17 (m, 1H), 8.44-8.53 (m, 1H), 8.77-8.87 (m, 1H)

MS ES$^+$: 407

Example 24: N-[(1S,2S)-2-[(6-Fluoro-1,3-benzothiazol-2-yl)amino]cyclopentyl]-3-(1H-1,2,3-triazol-1-yl)pyridine-2-carboxamide

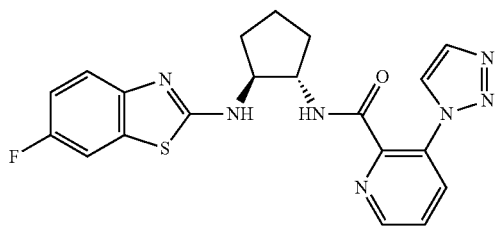

A microwave vial was charged with 3-bromo-N-[(1S,2S)-2-[(6-fluoro-1,3-benzothiazol-2-yl)amino]cyclopentyl]-pyridine-2-carboxamide (Example 1, 900 mg, 2.07 mmol), 2H-1,2,3-triazole (CAS number 288-36-8; 286 mg, 4.13 mmol), cesium carbonate (1347 mg, 4.13 mmol), copper (I) iodide (20 mg, 0.11 mmol) and trans-1-N,2-N-dimethylcyclohexane-1,2-diamine (59 mg, 0.41 mmol) in DMF (6.9 ml). The reaction mixture was subjected to microwave irradiation at 120° C. for 1 hour then partitioned between ethyl acetate and water. The organics were washed with water and brine, dried over magnesium sulfate, filtered and concentrated in vacuo. The crude material was purified by column chromatography (silica, 50-100% ethyl acetate/petrol then 0-30% methanol/ethyl acetate) then purified further by column chromatography (silica, 50-100% ethyl acetate/petrol then 0-20% methanol/ethyl acetate). The resultant material was recrystallised from ethyl acetate to afford the title compound.

$^1$H NMR (400 MHz, DMSO-d$_6$) δ ppm 1.48-1.64 (m, 2H), 1.65-1.75 (m, 2H), 2.01-2.17 (m, 2H), 4.08-4.16 (m, 1H), 4.16-4.25 (m, 1H), 6.96-7.11 (m, 1H), 7.30-7.41 (m, 1H), 7.54-7.65 (m, 1H), 7.67-7.75 (m, 1H), 8.05 (s, 2H), 8.10-8.18 (m, 1H), 8.20-8.30 (m, 1H), 8.61-8.72 (m, 1H), 8.77-8.86 (m, 1H)

MS ES$^+$: 424

Example 25: N-[(1S,2S)-2-[(6-Chloro-1,3-benzoxazol-2-yl)amino]cyclopentyl]-3-(difluoromethoxy)pyridine-2-carboxamide

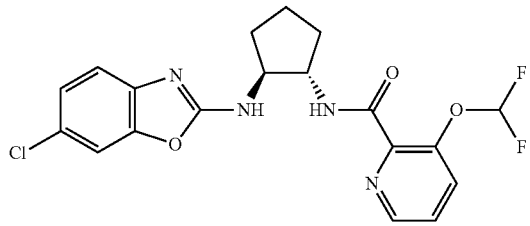 [SMILES: O=C(N[C@H]1CCC[C@@H]1Nc1nc2ccc(Cl)cc2s1)c1ncccc1OC(F)F]

To a solution of N-[(1S,2S)-2-aminocyclopentyl]-2-(difluoromethoxy)benzamide hydrochloride (Intermediate 11; 49 mg, 0.16 mmol) in DMSO (0.5 ml) was added DIPEA (0.083 ml, 0.48 mmol) and 2,6-dichloro-1,3-benzoxazole (CAS number 3621-82-7; 36 mg, 0.19 mmol). The reaction mixture was heated at 140° C. for 4 hours then partitioned between ethyl acetate and water. The organics were washed with water and brine, dried over sodium sulfate and concentrated in vacuo. The crude material was purified by reverse phase chromatography (C18 silica, 0-100% water (with 0.05% ammonia)/acetonitrile) then further purified by column chromatography (basic silica, 0-35% ethyl acetate/petrol) to afford the title compound.

$^1$H NMR (400 MHz, DMSO-d$_6$) δ ppm 1.53-1.68 (m, 2H), 1.68-1.81 (m, 2H), 2.03-2.18 (m, 2H), 4.07-4.21 (m, 1H), 4.23-4.34 (m, 1H), 6.86-7.36 (m, 3H), 7.43-7.51 (m, 1H), 7.55-7.65 (m, 1H), 7.68-7.79 (m, 1H), 8.17-8.31 (m, 1H), 8.41-8.53 (m, 1H), 8.72-8.84 (m, 1H)

MS ES$^+$: 423

Example 26: 3-Ethoxy-6-methyl-N-[2-(quinolin-2-ylmethyl)cyclopentyl]pyridine-2-carboxamide

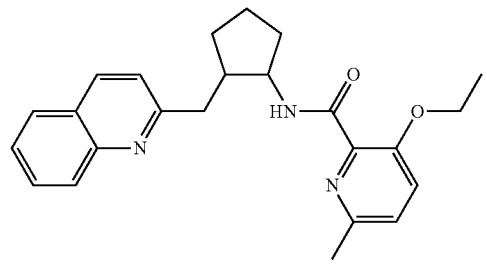 [SMILES: CCOc1ccc(C)nc1C(=O)NC1CCCC1Cc1ccc2ccccc2n1]

To a solution of 2-(quinolin-2-ylmethyl)cyclopentan-1-amine hydrochloride (Intermediate 12, Isomer 1; 75 mg, 0.29 mmol) in DCM (950 μl) was added 3-ethoxy-6-methylpyridine-2-carboxylic acid (Intermediate 13; 57 mg, 0.32 mmol), EDC (60 mg, 0.31 mmol), 3H-[1,2,3]triazolo[4,5-b]pyridin-3-ol (43 mg, 0.32 mmol) and DIPEA (150 μl, 0.86 mmol). The reaction mixture was stirred at room temperature for 24 hours. The reaction mixture was washed with water, filtered through a hydrophobic frit and concentrated in vacuo. The crude material was purified by column chromatography (silica, 50-100% ethyl acetate/petrol, then 0-20% methanol/ethyl acetate) to afford the title compound.

$^1$H NMR (400 MHz, DCM-d$_2$) δ ppm 1.45-1.53 (m, 3H), 1.54-1.62 (m, 1H), 1.65-1.93 (m, 4H), 2.04-2.19 (m, 1H), 2.53 (s, 3H), 2.70-2.82 (m, 1H), 2.88-3.02 (m, 1H), 3.21-

3.36 (m, 1H), 4.04-4.23 (m, 2H), 4.54-4.67 (m, 1H), 7.19-7.25 (m, 1H), 7.26-7.31 (m, 1H), 7.35-7.42 (m, 1H), 7.49-7.57 (m, 1H), 7.66-7.73 (m, 1H), 7.79-7.86 (m, 1H), 7.94-8.03 (m, 1H), 8.08-8.17 (m, 1H)

MS ES$^+$: 390

Example 27: 3-Ethoxy-6-methyl-N-[2-(quinolin-2-ylmethyl)cyclopentyl]pyridine-2-carboxamide

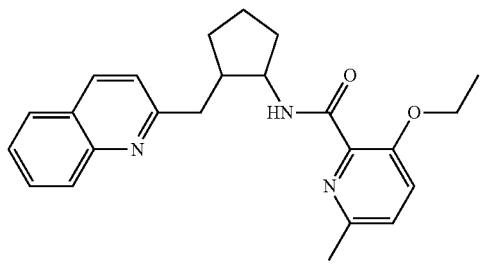 [SMILES: CCOc1ccc(C)nc1C(=O)NC1CCCC1Cc1ccc2ccccc2n1]

To a solution of 3-ethoxy-6-methylpyridine-2-carboxylic acid (Intermediate 13; 51 mg, 0.29 mmol) in DMF (3 ml) was added DIPEA (0.15 g, 1.14 mmol), TBTU (0.11 g, 0.34 mmol) and 2-(quinolin-2-ylmethyl)cyclopentan-1-amine hydrochloride (Intermediate 12, Isomer 2; 75 mg, 0.29 mmol). The reaction mixture was stirred at room temperature for 5 hours then poured into water and extracted with ethyl acetate. The organics were washed with brine, dried over sodium sulfate, filtered and concentrated in vacuo. The crude material was purified by column chromatography (silica, 0-70% ethyl acetate/n-hexane) to afford the title compound.

$^1$H NMR (400 MHz, DMSO-d) δ ppm 1.24-1.27 (m, 3H), 1.32-1.36 (m, 1H), 1.50-1.67 (m, 4H), 1.99-2.01 (m, 1H), 2.33-2.39 (m, 4H), 2.75-2.81 (m, 1H), 3.26-3.27 (m, 1H), 4.00-4.05 (m, 3H), 7.22-7.28 (m, 1H), 7.41-7.45 (m, 2H), 7.51-7.55 (m, 1H), 7.68-7.72 (m, 1H), 7.91-7.96 (m, 2H), 8.24-8.30 (m, 2H)

MS ES$^+$: 390

3. BIOLOGICAL EFFICACY OF COMPOUNDS OF THE INVENTION

Orexin antagonist activity was determined by measuring changes in intracellular calcium levels using a Ca$^{2+}$ sensitive fluorescent dye. The changes in fluorescent signal were monitored by Fluorescent Imaging Plate Reader (FLIPR™) technology available from Molecular Devices, LLC, U.S.A. Orexin mediated increases in intracellular Ca$^{2+}$ concentration were readily detected upon activation with orexin-A. Twenty-four hours prior to the assay, RBL-2H3 cells stably expressing either human orexin receptor 1 or human orexin receptor 2 were seeded in cell culture medium in black, clear-bottom 384-well plates (commercially available from Corning Inc., U.S.A.) and grown overnight at 37° C., 5% CO$_2$. On the day of the assay, cell culture media was removed and cells were loaded with Calcium 5 Dye (commercially sold by Molecular Devices, LLC, U.S.A.) for 1 hour at 37° C., 5% CO$_2$. Test compounds (at 10 point half log concentration response curves from 10 μM) were added to cells for 15 minutes prior to the addition of orexin-A to all wells, to achieve a final concentration that produces approximately an 80% maximal response. The IC$_{50}$ values were determined from ten point concentration response curves. Curves were generated using the average of two wells for each data point. The results obtained are shown in the table below in which 'NT' denotes 'Not Tested'.

Results

| Example Number | Human Orexin1R IC$_{50}$ (nM) | Human Orexin2R IC$_{50}$ (nM) |
| --- | --- | --- |
| 1 | 43 | >10,000 |
| 2 | 128 | NT |
| 3 | 170 | >10,000 |
| 4 | NT | NT |
| 5 | 14 | 2800 |
| 6 | 8.6 | >10,000 |
| 7 | 540 | >10,000 |
| 8 | 34 | 3300 |
| 9 | 84 | >10,000 |
| 10 | 21 | >10,000 |
| 11 | 330 | >10,000 |
| 12 | 42 | >10,000 |
| 13 | 69 | >10,000 |
| 14 | 170 | >10,000 |
| 15 | 150 | >10,000 |
| 16 | 630 | NT |
| 17 | 210 | 9600 |
| 18 | 41 | 8800 |
| 19 | 33 | 3600 |
| 20 | 100 | >10,000 |
| 21 | 24 | >10,000 |
| 22 | 300 | >10,000 |
| 23 | 290 | >10,000 |
| 24 | 86 | >10,000 |
| 25 | 660 | >10,000 |
| 26 | 910 | NT |
| 27 | 71 | 6000 |

The invention claimed is:

1. A compound of formula

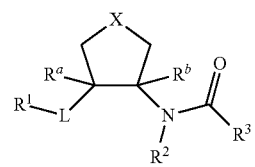

wherein
R$^1$ represents an 8- to 10-membered fused bicyclic heteroaromatic group optionally substituted by at least one substituent independently selected from halogen, cyano, hydroxyl, C$_3$-C$_6$ cycloalkyl, C$_1$-C$_3$ alkyl, C$_1$-C$_3$ alkoxy, C$_1$-C$_3$ alkoxycarbonyl, C$_1$-C$_3$ alkoxycarbonylamino, C$_1$-C$_3$ haloalkoxy, —NR$^4$R$^5$, C$_3$-C$_6$ cycloalkylamino, C$_1$-C$_3$ alkylcarbonyloxy, C$_1$-C$_3$ alkylcarbonylamino, sulphonamido, C$_1$-C$_3$ alkylsulphonyl, C$_1$-C$_3$ alkylsulphonylamino and —C(O)NR$^6$R$^7$;

L represents a bond, CH$_2$, O, NH or N(CH$_3$);

R$^a$ represents a hydrogen atom or a C$_1$-C$_3$ alkyl or C$_1$-C$_3$ haloalkyl group;

R$^b$ represents a hydrogen atom or a C$_1$-C$_3$ alkyl or C$_1$-C$_3$ haloalkyl group;

X represents CF$_2$, CHR$^8$;

R$^2$ represents a hydrogen atom or a C$_1$-C$_6$ alkyl or C$_3$-C$_6$ cycloalkyl group;

R$^3$ represents a 5- or 6-membered monocyclic heteroaromatic group optionally substituted by at least one substituent independently selected from halogen, hydroxyl, cyano, C$_1$-C$_3$ alkyl, C$_1$-C$_3$ haloalkyl, C₁-C₃ hydroxyalkyl, C₁-C₃ alkoxy, C₁-C₃ haloalkoxy, C₂-C₄ alkenyl, C₁-C₃ alkylcarbonyloxy, C₁-C₃ alkoxycarbonyl, —NR$^{10}$R$^{11}$, —C(O)NR$^{12}$R$^{13}$, C₃-C₆ cycloalkyl, C₃-C₆ cycloalkyloxy, C₃-C₆ cycloalkylmethyl or a 5- or 6-membered heteroaryl group, the heteroaryl group being optionally substituted by at least one substituent independently selected from C₁-C₆ alkyl, C₁-C₆ alkoxy and C₁-C₆ haloalkoxy;

R$^4$ and R$^5$ each independently represent a hydrogen atom or a C₁-C₃ alkyl or C₃-C₆ cycloalkyl group, or R$^4$ and R$^5$ may together with the nitrogen atom to which they are attached form a 4- to 7-membered saturated heterocyclic ring optionally substituted by at least one substituent independently selected from halogen, hydroxyl and C₁-C₃ alkoxy;

R$^6$ and R$^7$ each independently represent a hydrogen atom or a C₁-C₃ alkyl or C₃-C₆ cycloalkyl group, or R$^6$ and R$^7$ may together with the nitrogen atom to which they are attached form a 4- to 7-membered saturated heterocyclic ring optionally substituted by at least one substituent independently selected from halogen and hydroxyl;

R$^8$ represents a hydrogen or halogen atom or a hydroxyl group;

R$^{10}$ and R$^{11}$ each independently represent a hydrogen atom or a C₁-C₃ alkyl or C₃-C₆ cycloalkyl group, or R$^{10}$ and R$^{11}$ may together with the nitrogen atom to which they are attached form a 4- to 7-membered saturated heterocyclic ring optionally substituted by at least one substituent independently selected from halogen, hydroxyl and C₁-C₃ alkoxy; and R$^{12}$ and R$^{13}$ each independently represent a hydrogen atom or a C₁-C₃ alkyl or C₃-C₆ cycloalkyl group, or R$^{12}$ and R$^{13}$ may together with the nitrogen atom to which they are attached form a 4- to 7-membered saturated heterocyclic ring optionally substituted by at least one substituent independently selected from halogen and hydroxyl;

or a pharmaceutically acceptable salt thereof.

2. A compound according to claim 1, wherein R$^1$ represents a 9- or 10-membered fused bicyclic heteroaromatic group containing one or two ring heteroatoms independently selected from nitrogen, oxygen and sulphur, the heteroaromatic group being optionally substituted by one or more halogen atoms.

3. A compound according to claim 1, wherein R$^1$ represents a 9- or 10-membered fused bicyclic heteroaromatic group selected from quinoxalinyl, benzothiazolyl, benzoxazolyl, quinolinyl and quinazolinyl, all optionally substituted as claimed in claim 1.

4. A compound according to claim 1, wherein X represents CH₂.

5. A compound according to claim 1, wherein L represents NH.

6. A compound according to claim 1, wherein R$^2$ represents a hydrogen atom or methyl group.

7. A compound according to claim 1, wherein R$^3$ represents a 5- or 6-membered monocyclic heteroaromatic group selected from pyridinyl, pyrimidinyl and pyrazinyl, all optionally substituted as claimed in claim 1.

8. A compound according to claim 1, wherein R$^3$ is optionally substituted by at least one substituent independently selected from fluorine, chlorine, bromine, C₁-C₃ alkyl, C₁-C₃ alkoxy, C₁-C₃ haloalkyl, C₁-C₃ haloalkoxy, —NR$^{10}$R$^{11}$, or a 5- or 6-membered heteroaryl group, the heteroaryl group being optionally substituted by one or two substituents independently selected from C₁-C₂ alkyl, C₁-C₂ alkoxy and C₁-C₂ haloalkoxy.

9. A compound according to claim 1, wherein R$^3$ is optionally substituted by at least one 5- or 6-membered heteroaryl group selected from triazolyl, pyrazolyl, oxadiazolyl, pyrimidinyl and imidazolyl, all optionally substituted by one or two substituents independently selected from C₁-C₂ alkyl.

10. A compound of formula (I) as claimed in claim 1 selected from the group consisting of:

3-Bromo-N-[(1S,2S)-2-[(6-fluoro-1,3-benzothiazol-2-yl)amino] cyclopentyl]-pyridine-2-carboxamide;

6-Bromo-N-[(1S,2S)-2-[(6-fluoro-1,3-benzothiazol-2-yl)amino] cyclopentyl]-3-methoxypyridine-2-carboxamide;

N-[(1S,2S)-2-[(6-Fluoro-1,3-benzothiazol-2-yl)amino] cyclopentyl]-3-methoxypyridine-2-carboxamide;

3-Chloro-N-[(1S,2S)-2-[(6-fluoro-1,3-benzothiazol-2-yl)amino] cyclopentyl]-pyridine-2-carboxamide;

N-[(1S,2S)-2-[(6-Fluoro-1,3-benzothiazol-2-yl)amino] cyclopentyl]-3-methoxy-N-methylpyridine-2-carboxamide;

N-[(1S,2S)-2-[(6-Fluoro-1,3-benzothiazol-2-yl)amino] cyclopentyl]-3-(2H-1,2,3-triazol-2-yl)pyridine-2-carboxamide;

N-[(1S,2S)-2-[(6-Fluoro-1,3-benzoxazol-2-yl)amino]cyclopentyl]-3-methoxypyridine-2-carboxamide;

N-[(1S,2S)-2-[(6-Fluoro-1,3-benzothiazol-2-yl)amino] cyclopentyl]-3-(propan-2-yloxy)pyridine-2-carboxamide;

N-[(1S,2S)-2-[(6-Fluoro-1,3-benzothiazol-2-yl)amino] cyclopentyl]-3-methoxy-6-methylpyridine-2-carboxamide;

N-[(1S,2S)-2-[(6-Fluoro-1,3-benzothiazol-2-yl)amino] cyclopentyl]-3-(1H-pyrazol-1-yl)pyridine-2-carboxamide;

3-Fluoro-N-[(1S,2S)-2-[(6-fluoro-1,3-benzothiazol-2-yl)amino]cyclopentyl]pyridine-2-carboxamide;

N-[(1S,2S)-2-[(6-Fluoro-1,3-benzothiazol-2-yl)amino] cyclopentyl]-3-(piperidin-1-yl)pyridine-2-carboxamide;

3-(Azetidin-1-yl)-N-[(1S,2S)-2-[(6-fluoro-1,3-benzothiazol-2-yl)amino]cyclopentyl]pyridine-2-carboxamide;

N-[(1S,2S)-2-[(6-Fluoro-1,3-benzothiazol-2-yl)amino] cyclopentyl]-3-(pyrrolidin-1-yl)pyridine-2-carboxamide;

N-[(1S,2S)-2-[(6-Fluoro-1,3-benzothiazol-2-yl)amino] cyclopentyl]-3-(3-methoxyazetidin-1-yl)pyridine-2-carboxamide;

3-Methoxy-N-[(1S,2S)-2-[(quinoxalin-2-yl)amino]cyclopentyl]pyridine-2-carboxamide;

N-[(1S,2S)-2-[(6-Fluoro-1,3-benzothiazol-2-yl)amino] cyclopentyl]-3-methoxy-6-(trifluoromethyl)pyridine-2-carboxamide;

3-Ethoxy-N-[(1S,2S)-2-[(6-fluoro-1,3-benzothiazol-2-yl)amino]cyclopentyl]pyridine-2-carboxamide;

N-[(1S,2S)-2-[(6-Fluoro-1,3-benzothiazol-2-yl)amino] cyclopentyl]-3-(trifluoromethoxy)pyridine-2-carboxamide;

3-(Difluoromethoxy)-N-[(1S,2S)-2-[(6-fluoro-1,3-benzothiazol-2-yl)amino]cyclopentyl]pyridine-2-carboxamide;

N-[(1S,2S)-2-[(6-Chloro-1,3-benzothiazol-2-yl)amino] cyclopentyl]-3-(2H-1,2,3-triazol-2-yl)pyridine-2-carboxamide;

N-[(1S,2S)-2-[(6-Chloro-1,3-benzothiazol-2-yl)amino]cyclopentyl]-3-(difluoromethoxy)pyridine-2-carboxamide;

3-(Difluoromethoxy)-N-[(1S,2S)-2-[(6-fluoro-1,3-benzoxazol-2-yl)amino]cyclopentyl]pyridine-2-carboxamide;

N-[(1S,2S)-2-[(6-Fluoro-1,3-benzothiazol-2-yl)amino]cyclopentyl]-3-(1H-1,2,3-triazol-1-yl)pyridine-2-carboxamide;

N-[(1S,2S)-2-[(6-Chloro-1,3-benzoxazol-2-yl)amino]cyclopentyl]-3-(difluoromethoxy)pyridine-2-carboxamide;

3-Ethoxy-6-methyl-N-[2-(quinolin-2-ylmethyl)cyclopentyl]pyridine-2-carboxamide;

3-Ethoxy-6-methyl-N-[2-(quinolin-2-ylmethyl)cyclopentyl]pyridine-2-carboxamide;

enantiomers thereof and pharmaceutically acceptable salts of any of the foregoing.

11. A pharmaceutical composition comprising a compound of formula (I) or a pharmaceutically acceptable salt thereof as claimed in claim 1, in association with a pharmaceutically acceptable adjuvant, diluent or carrier, and optionally one or more other therapeutic agents.

12. A composition according to claim 11, wherein the one or more other therapeutic agents are selected from carbamazepine, olanzapine, quetiapine, verapamil, lamotrigine, oxcarbazepine, risperidone, aripiprazole, ziprasidone and lithium.

* * * * *